(12) United States Patent
Stahl et al.

(10) Patent No.: US 10,892,064 B2
(45) Date of Patent: Jan. 12, 2021

(54) MULTI-LEAF COLLIMATOR

(71) Applicant: SHANGHAI UNITED IMAGING HEALTHCARE CO., LTD., Shanghai (CN)

(72) Inventors: Johannes Stahl, Concord, CA (US); Jonathan Maltz, Concord, CA (US)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/210,124

(22) Filed: Dec. 5, 2018

(65) Prior Publication Data

US 2020/0185119 A1      Jun. 11, 2020

(51) Int. Cl.
*G21K 1/04*       (2006.01)
*A61N 5/10*       (2006.01)

(52) U.S. Cl.
CPC .......... *G21K 1/046* (2013.01); *A61N 5/1047* (2013.01)

(58) Field of Classification Search
CPC ......... A61N 5/1047; G21K 1/046; G21K 1/04
See application file for complete search history.

(56) References Cited

U.S. PATENT DOCUMENTS

| 5,754,623 | A | 5/1998 | Seki | |
| 8,384,049 | B1* | 2/2013 | Broad | G21K 1/046 |
| | | | | 250/492.1 |
| 2002/0101959 | A1* | 8/2002 | Kato | A61N 5/1042 |
| | | | | 378/152 |
| 2006/0256915 | A1 | 11/2006 | Otto et al. | |
| 2007/0016014 | A1 | 1/2007 | Hara et al. | |
| 2007/0164239 | A1* | 7/2007 | Terwilliger | G21K 1/046 |
| | | | | 250/505.1 |
| 2008/0292058 | A1* | 11/2008 | Nagata | G21K 1/04 |
| | | | | 378/152 |
| 2009/0251709 | A1 | 10/2009 | Kindlein | |
| 2010/0202588 | A1 | 8/2010 | Shibuya et al. | |
| 2010/0208274 | A1 | 8/2010 | Kindlein et al. | |
| 2010/0278310 | A1* | 11/2010 | Dehler | G21K 1/04 |
| | | | | 378/150 |
| 2012/0008744 | A1 | 1/2012 | Bani-Hashemi | |

(Continued)

FOREIGN PATENT DOCUMENTS

| WO | 2016000777 A1 | 1/2016 |
| WO | 2018031365 A1 | 2/2018 |

(Continued)

OTHER PUBLICATIONS

International Search Report in PCT/CN2018/085279 dated Jan. 23, 2019, 5 Pages.

(Continued)

*Primary Examiner* — Nicole M Ippolito
*Assistant Examiner* — Sean M Luck
(74) *Attorney, Agent, or Firm* — Metis IP LLC

(57) ABSTRACT

A multi-leaf collimator is provided. The multi-leaf collimator may include a plurality of leaves configured to shield radiation beams. At least two leaves of the plurality of leaves may be movable in a direction parallel to each another. Each leaf of at least some of the plurality of leaves may be configured to be movable between at least two positions. At least one of the at least two positions may be adjustable.

20 Claims, 14 Drawing Sheets

(56) References Cited

U.S. PATENT DOCUMENTS

| | | | | |
|---|---|---|---|---|
| 2012/0043482 A1* | 2/2012 | Prince | ............... | A61N 5/1045 |
| | | | | 250/505.1 |
| 2013/0301893 A1 | 11/2013 | Netsch et al. | | |
| 2014/0217312 A1* | 8/2014 | Echner | ............... | A61N 5/1045 |
| | | | | 250/505.1 |
| 2014/0239204 A1* | 8/2014 | Orton | ............... | G21K 1/046 |
| | | | | 250/505.1 |
| 2015/0170778 A1* | 6/2015 | Echner | ............... | G21K 1/046 |
| | | | | 250/505.1 |
| 2016/0271423 A1 | 9/2016 | Takahashi | | |
| 2016/0361566 A1* | 12/2016 | Larkin | ............... | A61N 5/1045 |
| 2017/0281972 A1* | 10/2017 | Zhang | ............... | A61B 6/06 |
| 2018/0078789 A1 | 3/2018 | Ollila et al. | | |

FOREIGN PATENT DOCUMENTS

| | | |
|---|---|---|
| WO | 2019210455 A1 | 11/2019 |
| WO | 2019210456 A1 | 11/2019 |

OTHER PUBLICATIONS

Written Opinion in PCT/CN2018/085279 dated Jan. 23, 2019, 5 Pages.
International Search Report in PCT/CN2018/085266 dated Jan. 30, 2019, 5 Pages.
Written Opinion in PCT/CN2018/085266 dated Jan. 30, 2019, 3 Pages.

* cited by examiner

1000

```
Actuating, by a second drive mechanism, a stop block of the      1010
MLC to move to a first reference position corresponding to a
first target position when radiation delivery is on
```

```
Holding, by a brake component of the MLC, the leaf back          1020
from moving when the stop block is moving
```

```
Actuating, by a first drive mechanism, the leaf to move to the   1030
first target position when the radiation delivery is off
```

FIG. 10

MULTI-LEAF COLLIMATOR

TECHNICAL FIELD

The present disclosure generally relates to radiation systems, and more specifically relates to radiation delivery devices including a multi-leaf collimator, and systems and methods for controlling the multi-leaf collimator.

BACKGROUND

Radiotherapy has been widely employed in cancer treatment in which ionizing radiation is guided towards a treatment region (e.g., a tumor). Considerations of radiotherapy include that the tumor receives sufficient radiation, while the damage to an organ at risk (OAR) is minimized as much as possible during the radiotherapy. The tumor and/or the OAR may be in motion due to a physiological motion (e.g., respiratory motion, cardiac motion, muscle contraction, and relaxation) of the object under the treatment. The treatment region may change with such motion of the object. One solution is to design a radiation system capable of detecting the motion of the tumor and adjusting the radiation to the tumor region accordingly. In order to realize such radiation system, it is desirable that the gantry of the radiation system can rotate at a relatively high speed. When the gantry rotates at the relatively high speed, the multi-leaf collimator mounted on the gantry should also operate at a relatively high speed. Thus, it is desirable to provide a multi-leaf collimator in which the leaves thereof that can move at a relatively high speed during radiotherapy.

SUMMARY

In one aspect of the present disclosure, a multi-leaf collimator is provided. The multi-leaf collimator may include a plurality of leaves configured to shield radiation beams. In some embodiments, at least two leaves of the plurality of leaves may be movable in a direction parallel to each another. In some embodiments, one or more leaves of at least some of the plurality of leaves may be configured to be movable between at least two positions. In some embodiments, at least one of the at least two positions may be adjustable.

In another aspect of the present disclosure, a multi-leaf collimator is provided. The multi-leaf collimator may include a plurality of pairs of leaves configured to shield radiation beams; an actuator configured to drive at least one leaf of the plurality of pairs of leaves to translate among a first set of predefined positions at a first speed; a positioner non-synchronically movable along with the actuator among a second set of predefined positions at a second speed slower than the first speed; and/or a position holder releasably coupled with the at least one leaf. The positioner may be configured to place the at least one leaf at each of the first set of predefined positions. The position holder may be configured to maintain the at least one leaf at the each of the first set of predefined positions when the positioner is moving from a first predefined position of the second set of predefined positions to a second predefined position of the second set of predefined positions.

In yet another aspect of the present disclosure, a multi-leaf collimator is provided. The multi-leaf collimator may include a plurality of pairs of leaves configured to shield radiation beams; and/or a driving assembly configured to drive each leaf of the plurality of pairs of leaves to translate completely and substantially instantly from a first operative position to a second operative position.

In yet another aspect of the present disclosure, a multi-leaf collimator is provided. The multi-leaf collimator may include a plurality of pairs of leaves configured to shield radiation beams; and/or a driving assembly configured to drive each leaf of the plurality of pairs of leaves to translate from a first position where the plurality of pairs of leaves form a first aperture, to a second position where the plurality of pairs of leaves form a second aperture. In some embodiments, the first aperture may be changed to the second aperture non-gradually.

In yet another aspect of the present disclosure, a leaf module of a multi-leaf collimator is provided. The leaf module may include a leaf configured to shield a portion of radiation beams, the leaf being capable of moving between at least three positions; a first drive mechanism configured to actuate a movement of the leaf; a stop block configured to define the at least three positions of the leaf; and/or a second drive mechanism configured to actuate the stop block to move to define the at least three positions.

In yet another aspect of the present disclosure, a system for controlling a multi-leaf collimator is provided. The system may include at least one storage device including a set of instructions for controlling a movement of at least one leaf of the multi-leaf collimator; at least one processor in communication with the at least one storage device, wherein when executing the set of instructions, the at least one processor may be configured to cause the system to cause the at least one leaf of the multi-leaf collimator to move between one or more positions. To cause a leaf of the at least one leaf to move to a first target position of the one or more positions, the system may be caused to actuate, by a second drive mechanism, a stop block of the multi-leaf collimator to move to a first reference position corresponding to the first target position when radiation beams are on; and/or actuate, by a first drive mechanism, the leaf to move to the first target position when the radiation beams are off.

In yet another aspect of the present disclosure, a radiation system is provided. The radiation system may include a radiation source; and a multi-leaf collimator. The multi-leaf collimator may include a plurality of pairs of leaves configured to shield radiation beams emitted from the radiation source; and a driving assembly. The driving assembly may include a driving sub-assembly configured to drive each leaf of the plurality of pairs of leaves to translate completely and substantially instantly from a first operative position to a second operative position during the radiation beams are off; and a position holding sub-assembly configured to maintain the each leaf in the first operative position or the second operative position during the radiation beams are on.

In some embodiments, at least some of the plurality of leaves may be configured to move simultaneously while the radiation beams are off.

In some embodiments, a movement of at least one of the plurality of leaves from a first position to a second position may be actuated by compressed gas.

In some embodiments, a movement of at least one of the plurality of leaves from a first position to a second position may be actuated by a loaded spring.

In some embodiments, a movement of at least one of the plurality of leaves from a first position to a second position may be actuated by an electromagnetic motor.

In some embodiments, the multi-leaf collimator may further include a first drive mechanism configured to actuate a movement of the each leaf from a first position to a second position.

In some embodiments, the first drive mechanism may include at least one of a pneumatic drive mechanism, a spring-based drive mechanism, or an electric-charge-based mechanism.

In some embodiments, the multi-leaf collimator may further include a plurality of stop blocks corresponding to the plurality of leaves. Each stop block of the plurality of stop blocks may be configured to define a position of a corresponding leaf of the plurality of leaves.

In some embodiments, the each stop block may be movable, and each of the at least two positions of the corresponding leaf may be adjustable by moving the each stop block.

In some embodiments, the multi-leaf collimator may further include a second drive mechanism configured to actuate the plurality of stop blocks to move.

In some embodiments, the second drive mechanism may include a plurality of driving motors. Each driving motor may be configured to move at least one of the plurality of stop blocks to one or more target positions to define one or more positions of at least one corresponding leaf.

In some embodiments, the each driving motor may be configured to move at least one of the plurality of stop blocks while the radiation beams are on.

In some embodiments, the multi-leaf collimator may further include at least one brake component configured to keep one or more of the plurality of leaves from moving when the corresponding one or more stop blocks are moving.

In some embodiments, the multi-leaf collimator may further include a shield component configured to shield a first portion of the plurality of leaves such that a radiation beam is substantially blocked from passing through the first portion of the plurality of leaves.

In some embodiments, the multi-leaf collimator may be configured such that, when the radiation beam is on and the first portion of the plurality of leaves are shielded by the shield component, the first portion of the plurality of leaves may be actuated to move and a second portion of the plurality of leaves are held still to allow passage of the radiation beam.

In some embodiments, the multi-leaf collimator may further include a shield component configured to shield a first portion of the plurality of leaves or a second portion of the plurality of leaves. The shield component may be capable of switching between a first shielding position and a second shielding position. At the first shielding position the shield component may shield the first portion of the plurality of leaves. At the second shielding position the shield component may shield the second portion of the plurality of leaves.

In some embodiments, the positioner may include a motor configured to drive the positioner to move at the second speed.

In some embodiments, the driving assembly may include at least one of a pneumatic drive mechanism, a spring-based drive mechanism, or an electric-charge-based mechanism.

In some embodiments, the multi-leaf collimator may further include a plurality of stop blocks corresponding to the plurality of pairs of leaves. Each stop block of the plurality of stop blocks may be configured to define a position of a corresponding leaf of the plurality of pairs of leaves.

In some embodiments, the each stop block may be movable, and the first operative position or the second operative position may be adjustable by moving the each stop block.

In some embodiments, the multi-leaf collimator may further include a drive mechanism configured to actuate the plurality of stop blocks to move.

In some embodiments, the leaf may include a notch set on an edge of the leaf. The stop block may include a protruding part. The protruding part may be configured to be operably coupled with the notch of the leaf.

In some embodiments, the protruding part may be configured to extend into the notch of the leaf such that the protruding part of the stop block restricts a movement of the leaf.

In some embodiments, the notch of the leaf may be longer than the protruding part of the stop block.

In some embodiments, the stop block may include a notch set on an edge of the stop block, and the leaf may include a protruding part. The protruding part may be configured to be operably coupled with the notch of the stop block.

In some embodiments, the leaf module may further include a leaf guide configured to guide a movement of the leaf such that the leaf is capable of moving along the leaf guide.

In some embodiments, the leaf module may further include a brake component configured to keep the leaf from moving when the stop block moves.

In some embodiments, the leaf module may further include a block guide configured to guide a movement of the stop block.

In some embodiments, the first drive mechanism may include at least one of compressed gas, a loaded spring, or an electromagnetic motor.

In some embodiments, the second drive mechanism may include a driving motor.

In some embodiments, the leaf may be capable of moving while the radiation beams are off. The stop block may be capable of moving while the radiation beams are on.

In some embodiments, the first drive mechanism may be configured to actuate the leaf to move at a first speed. The second drive mechanism may be configured to actuate the stop block to move at a second speed lower than the first speed.

In some embodiments, the second drive mechanism may include a driving motor.

In some embodiments, the first drive mechanism may include at least one of compressed gas, a loaded spring, or an electromagnetic motor.

In some embodiments, the at least one processor may be further configured to cause the system to keep, by a brake component of the multi-leaf collimator, the leaf from moving when the stop block is moving.

In some embodiments, the at least one processor may be further configured to cause the system to shield the leaf by switching a shield component of the multi-leaf collimator; actuate, by the second drive mechanism, the stop block to move to a second reference position corresponding to a second target position when radiation beams are on; actuate, by the first drive mechanism, the leaf to move to the second target position when the radiation beams are on; and/or expose, by switching the shield component away from the leaf, the leaf to allow the passage of the radiation beams through the leaf.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10 is a flowchart illustrating an exemplary process for moving a leaf according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
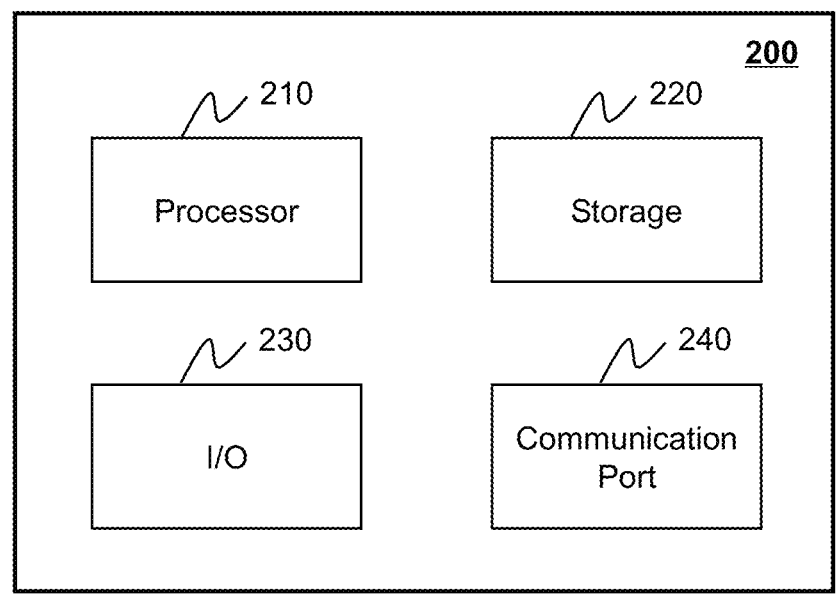
FIG. 2 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Some embodiments of the present disclosure may relate to a multi-leaf collimator (MLC). A conventional MLC actuated with motors and/or gears may offer a relatively low translation speed of the leaves of the MLC but a relatively high spatial resolution, while a binary MLC can be actuated much faster, it is desirable to combine the advantages of a conventional MLC and those of a binary MLC. In some embodiments, the MLC disclosed in the present disclosure may be configured as a combination of the characteristics of a conventional MLC and a binary MLC. The multi-leaf collimator disclosed in the present disclosure may include a plurality of leaves configured to shield radiation beams. At least two leaves of the plurality of leaves may be movable in a direction parallel to each. A leaf may be configured to be movable between at least two positions. At least one of the at least two positions may be adjustable. The MLC may include a plurality of stop blocks corresponding to the plurality of leaves. A stop block may be configured to define a position of a corresponding leaf of the plurality of leaves. The MLC may include a first drive mechanism configured to actuate a movement of a leaf from a first position to a second position. The MLC may further include a second drive mechanism configured to actuate the plurality of stop blocks to move. In the present disclosure, a leaf may be moved at a first speed (e.g., while radiation delivery is off), and the corresponding stop block of the leaf may be moved at a second speed lower than the first speed (e.g., while the radiation delivery is on). Thus, the off-period of the radiation delivery device may be shortened, the duty cycle (e.g., a ratio of an on-period to an off-period) of the radiation delivery device may be increased, the overall treatment time may be reduced, and the utilization efficiency of the radiation delivery device may be improved.

Figure 1:
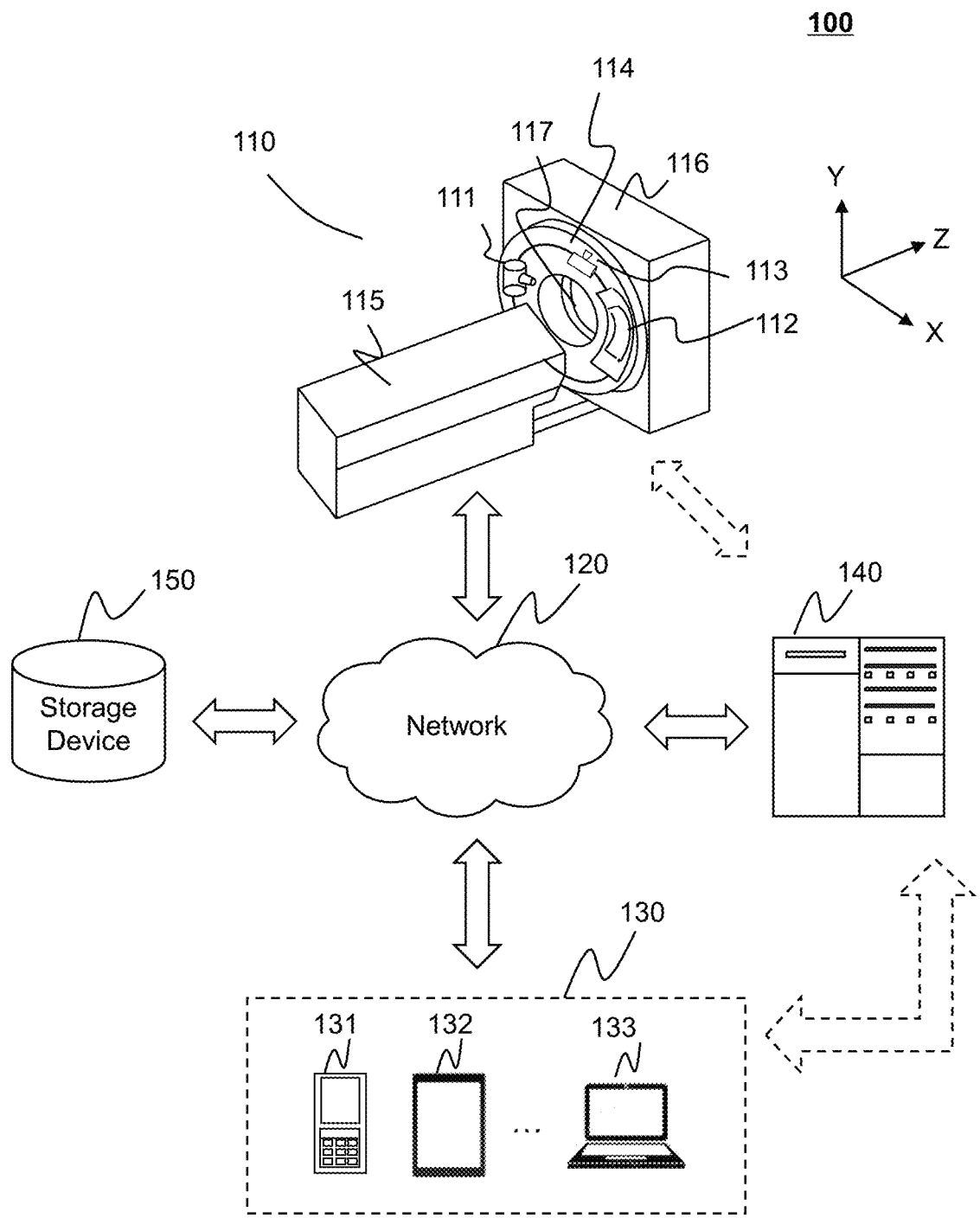
FIG. 1 is a schematic diagram illustrating an exemplary radiation system according to some embodiments of the present disclosure.

FIG. 1 is a schematic diagram illustrating an exemplary radiation system 100 according to some embodiments of the present disclosure. The radiation system 100 may include a radiation delivery device 110, a network 120, one or more terminals 130, a processing device 140, and a storage device 150. The components of the radiation system 100 may be connected in one or more of various ways. Merely by way of example, as illustrated in FIG. 1, the radiation delivery device 110 may be connected to the processing device 140 through the network 120. As another example, the radiation delivery device 110 may be connected to the processing device 140 directly as indicated by the bi-directional arrow in dotted lines linking the radiation delivery device 110 and the processing device 140. As a further example, the storage device 150 may be connected to the processing device 140 directly or through the network 120. As still a further example, one or more terminals 130 may be connected to the processing device 140 directly (as indicated by the bi-directional arrow in dotted lines linking the terminal(s) 130 and the processing device 140) or via the network 120.

In some embodiments, the radiation delivery device 110 may include only one radiation source (e.g., the first radiation source 113) for delivering radiotherapy. In some embodiments, the radiation delivery device 110 may include a first radiation source 113 and/or a second radiation source 111. The first radiation source 113 may emit a first beam toward a first region of an object (e.g., a patient or a portion thereof). The examples of the first radiation source 113 may be found elsewhere in this disclosure (e.g., treatment radiation source 430 illustrated in FIGS. 4A and 4B). The second radiation source 111 may emit a second beam toward a second region of the object. The examples of the second radiation source 111 may be found elsewhere in this disclosure (e.g., imaging radiation source 410 illustrated in FIG. 4A). In some embodiments, the first beam and the second beam may each include at least one radiation ray. The radiation ray may include but not limited to X-rays, $\alpha$-rays, $\beta$-rays, $\gamma$-rays, heavy ions, etc. Merely by way of example, the first radiation source may be a treatment radiation source, and the first region may correspond to a treatment region (e.g., a tumor); the second radiation source may be an imaging radiation source, and the second region may correspond to an imaging region including at least part of the treatment region. The intensity of the first beam may be the same as or different from the intensity of the second beam. For example, the energy of the first beam may be several megavolts (MV), this energy being greater than that of the second beam, which may be several kilovolts (kV). In some embodiments, the second radiation source 111 may be replaced by any other type of imaging device such as a computed tomography (CT) device, a magnetic resonance imaging (MRI) device, a positron emission tomography (PET) device, a single photon emission computed tomography (SPECT) device, or the like, or a combination thereof. More descriptions of the radiation delivery device 110 may be found elsewhere in the present disclosure (e.g., FIGS. 4A and 4B, and the descriptions thereof) and may be found in PCT Application No. PCT/CN2018/085266 entitled "RADIATION SYSTEMS FOR RADIATION TREATMENT AND IMAGING" filed May 2, 2018, and PCT Application No. PCT/CN2018/085279 entitled "SYSTEMS AND METHODS FOR GENERATING RADIATION TREATMENT PLAN" filed May 2, 2018, the contents of which are hereby incorporated by reference.

In some embodiments, the radiation delivery device 110 may further include a radiation detector 112 placed opposite to the second radiation source 111. In some embodiments, the radiation detector 112 may be mounted on a rotary ring 114. The radiation detector 112 may be configured to detect radiation emitted from the second radiation source 111. For example, the second beam emitted from the second radiation source 111 may transmit through (or be absorbed by) the object and attenuate when passing through the object. The radiation detector 112 may detect and/or receive radiation associated with at least a portion of the attenuated or scattered second beam.

In some embodiments, the radiation system 100 may include a gantry 116 to accommodate a bore 117 and a bed 115. The bed 115 may be a scanning bed or a treatment couch. The rotary ring 114 may be connected to the gantry 116. The bed 115 may be configured to support and/or transport the object (e.g., a patient) to the gantry 116 to be imaged and/or undergo radiotherapy.

It should be noted that the above descriptions of the radiation delivery device 110 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. For example, the radiation delivery device 110 may include the first radiation source 113 or the second radiation source 111 only. As another example, the first radiation source 113 and the second radiation source 111 may both be imaging radiation sources. Merely by way of example, a radiation detector may be mounted opposite to the first radiation source 113 on the rotary ring 114 configured to detect at least a portion of the first beam emitted from the first radiation source 113 (a portion of which may be attenuated when reaching the radiation detector). In some embodiments, the radiation delivery device 110 may further include one or more MLCs (not shown in FIG. 1). The MLC(s) may be configured to collimate radiation beam(s) of the radiation delivery device 110 and/or define the beam shape(s) thereof. An MLC may include multiple leaves. In some embodiments, the first radiation source 113 may include or be operably associated with an MLC. In some embodiments, the second radiation source 111 may include or be associated with an MLC.

The network 120 may include any suitable network that can facilitate the exchange of information and/or data for the radiation system 100. In some embodiments, one or more components of the radiation system 100 (e.g., the radiation delivery device 110, the terminal(s) 130, the processing device 140, or the storage device 150) may communicate information and/or data with one or more other components of the radiation system 100 via the network 120. For example, the processing device 140 may obtain data corresponding to radiation signals from the radiation delivery device 110 via the network 120. As another example, the processing device 140 may obtain user instructions from the terminal(s) 130 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or a combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 120 may include one or more network access points. For example, the network 120 may include wired and/or wireless network access points such as base stations and/or internet exchange points through which one or more components of the radiation system 100 may be connected to the network 120 to exchange data and/or information.

The terminal(s) 130 may include a mobile device 131, a tablet computer 132, a laptop computer 133, or the like, or a combination thereof. In some embodiments, the mobile device 131 may include a smart home device, a wearable device, a smart mobile device, a virtual reality device, an augmented reality device, or the like, or a combination thereof. In some embodiments, the smart home device may include a smart lighting device, a control device of an intelligent electrical device, a smart monitoring device, a smart television, a smart video camera, an interphone, or the like, or a combination thereof. In some embodiments, the wearable device may include a smart bracelet, smart footgear, a pair of smart glasses, a smart helmet, a smartwatch, smart clothing, a smart backpack, a smart accessory, or the like, or a combination thereof. In some embodiments, the smart mobile device may include a smartphone, a personal digital assistant (PDA), a gaming device, a navigation device, a point of sale (POS) device, or the like, or a combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or a combination thereof. For example, the virtual reality device and/or the augmented reality device may include a Google Glass, an Oculus Rift, a Hololens, a Gear VR, etc. In some embodiments, the terminal(s) 130 may remotely operate the radiation delivery device 110. In some embodiments, the terminal(s) 130 may operate the radiation delivery device 110 via a wireless connection. In some embodiments, the terminal(s) 130 may receive information and/or instructions inputted by a user, and send the received information and/or instructions to the radiation delivery device 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted.

The processing device 140 may process data and/or information obtained from the radiation delivery device 110, the terminal(s) 130, and/or the storage device 150. For example, the processing device 140 may process data corresponding to radiation signals of one or more detectors obtained from the radiation delivery device 110 and/or reconstruct an image of the object. The processing device 140 may obtain a treatment plan from the terminal (s), and/or the storage device 150 via the network 120. The treatment plan may correspond to a certain arrangement of the radiation delivery device 110 or components thereof. The treatment plan may include a plurality of radiation segments. Each radiation segment may be characterized by one or more parameters associated with an MLC, for example, a segment shape defined by a shape of an aperture formed by the MLC.

In some embodiments, the processing device 140 may be a single server or a server group. The server group may be centralized or distributed. In some embodiments, the processing device 140 may be local or remote. For example, the processing device 140 may access information and/or data stored in the radiation delivery device 110, the terminal(s) 130, and/or the storage device 150 via the network 120. As another example, the processing device 140 may be directly connected to the radiation delivery device 110, the terminal (s) 130, and/or the storage device 150 to access stored information and/or data. As a further example, the processing device 140 may be integrated into the radiation delivery device 110. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal(s) 130 and/or the processing device 140. For example, the storage device 150 may store a treatment plan, parameters, and/or the like. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or a combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or a combination thereof.

In some embodiments, the storage device 150 may be connected to the network 120 to communicate with one or more components of the radiation system 100 (e.g., the processing device 140, the terminal(s) 130, etc.). One or more components of the radiation system 100 may access the data or instructions stored in the storage device 150 via the network 120. In some embodiments, the storage device 150 may be directly connected to or communicate with one or more components of the radiation system 100 (e.g., the processing device 140, the terminal(s) 130, etc.). In some embodiments, the storage device 150 may be part of the processing device 140.

In some embodiments, the storage device 150 may include a set of instructions for controlling a movement of at least one leaf of the multi-leaf collimator (MLC). In some embodiments, the processing device 140 may include at least one processor in communication with the storage device 150. In some embodiments, when executing the set of instructions, the at least one processor may be configured to cause the system to cause the at least one leaf of the multi-leaf collimator to move between one or more positions. In some embodiments, to cause a leaf of the at least one leaf to move to a first target position of the one or more positions, the system may be caused to actuate, by a second drive mechanism, a stop block of the multi-leaf collimator to move to a first reference position corresponding to the first target position when radiation beams are on; and actuate, by a first drive mechanism, the leaf to move to the first target position when the radiation beams are off.

FIG. 2 is a schematic diagram illustrating hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include, for example, routines, programs, objects, components, signals, data structures, procedures, modules, and functions, which perform particular functions described herein. For example, the processor 210 may process data obtained from the radiation delivery device 110, the terminal(s) 130, the storage device 150, and/or any other component of the radiation system 100. In some embodiments, the processor 210 may perform instructions obtained from the terminal(s) 130. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof. Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the radiation delivery device 110, the terminal 130, the storage device 150, or any other component of the radiation system 100. In some embodiments, the storage 220 may include a mass storage device, a removable storage device, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for reducing or removing one or more artifacts in an image.

The I/O 230 may input or output signals, data, and/or information. In some embodiments, the I/O 230 may enable user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation delivery device 110, the terminal 130, or the storage device 150. The connection may be a wired connection, a wireless connection, or a combination of both that enables data transmission and reception. The wired connection may include an electrical cable, an optical cable, a telephone wire, or the like, or a combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
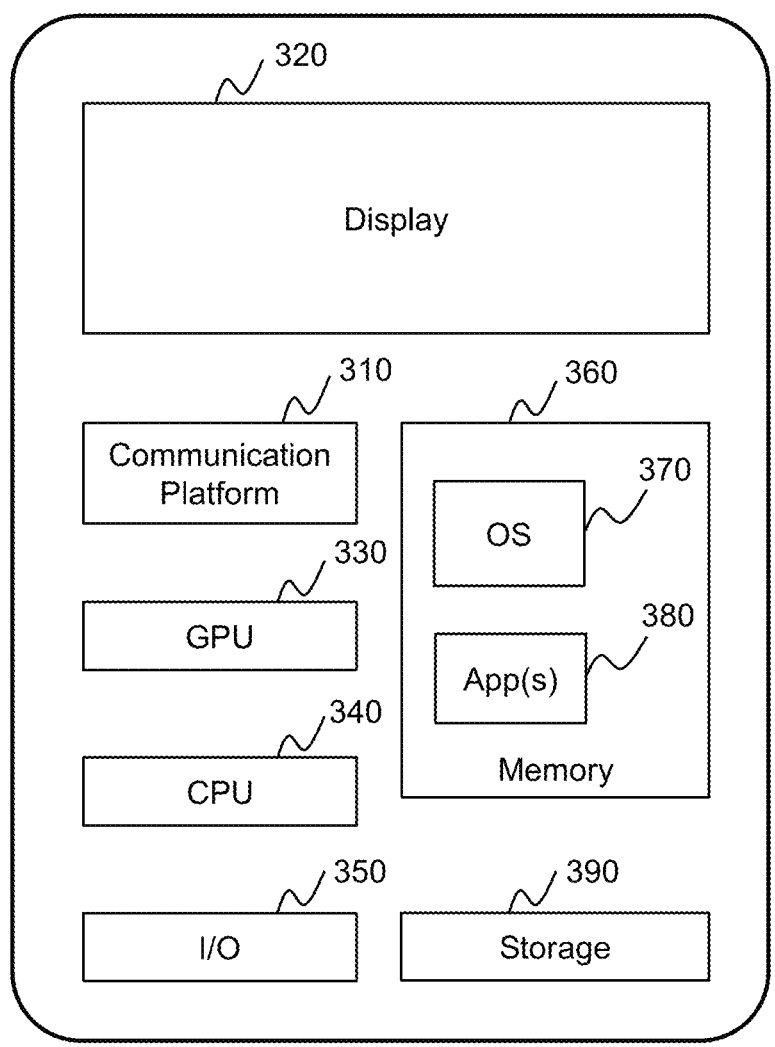
FIG. 3 is a schematic diagram illustrating hardware and/or software components of an exemplary mobile device according to some embodiments of the present disclosure.

FIG. 3 is a schematic diagram illustrating hardware and/or software components of an exemplary mobile device 300 according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiation system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to radiation systems for treatment and imaging as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4A:
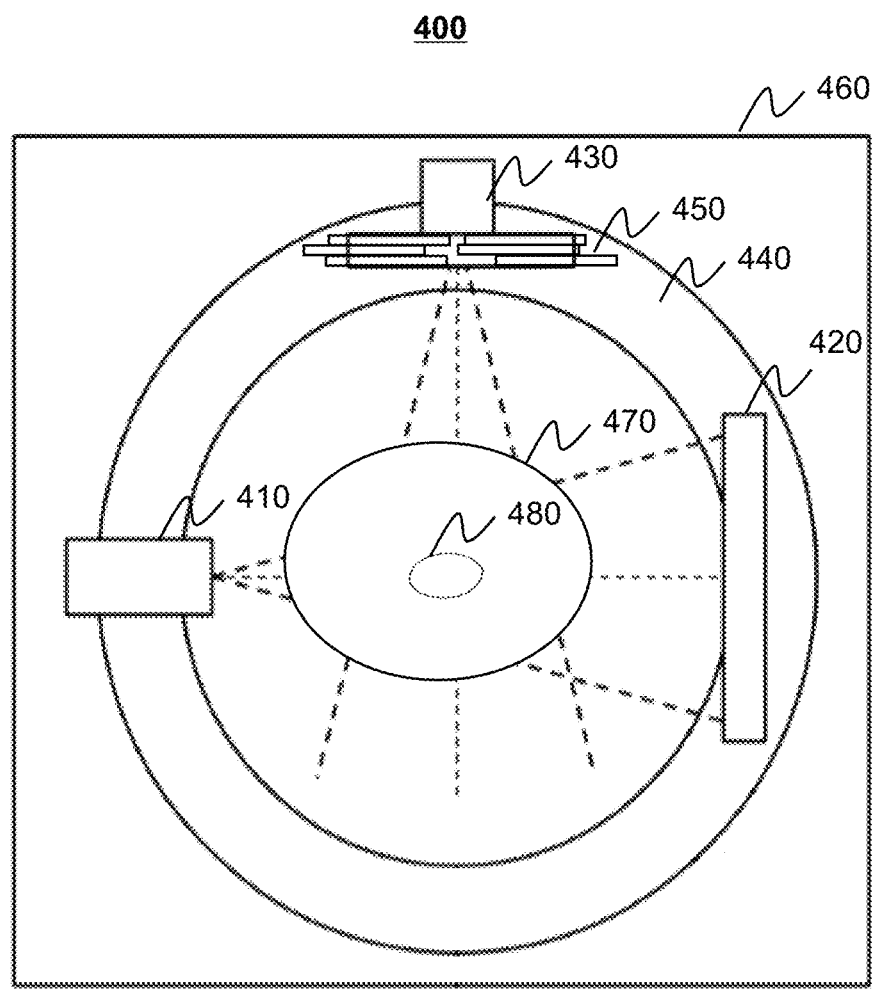
FIGS. 4A and 4B are schematic diagrams illustrating an exemplary radiation delivery device according to some embodiments of the present disclosure.
Figure 4B:
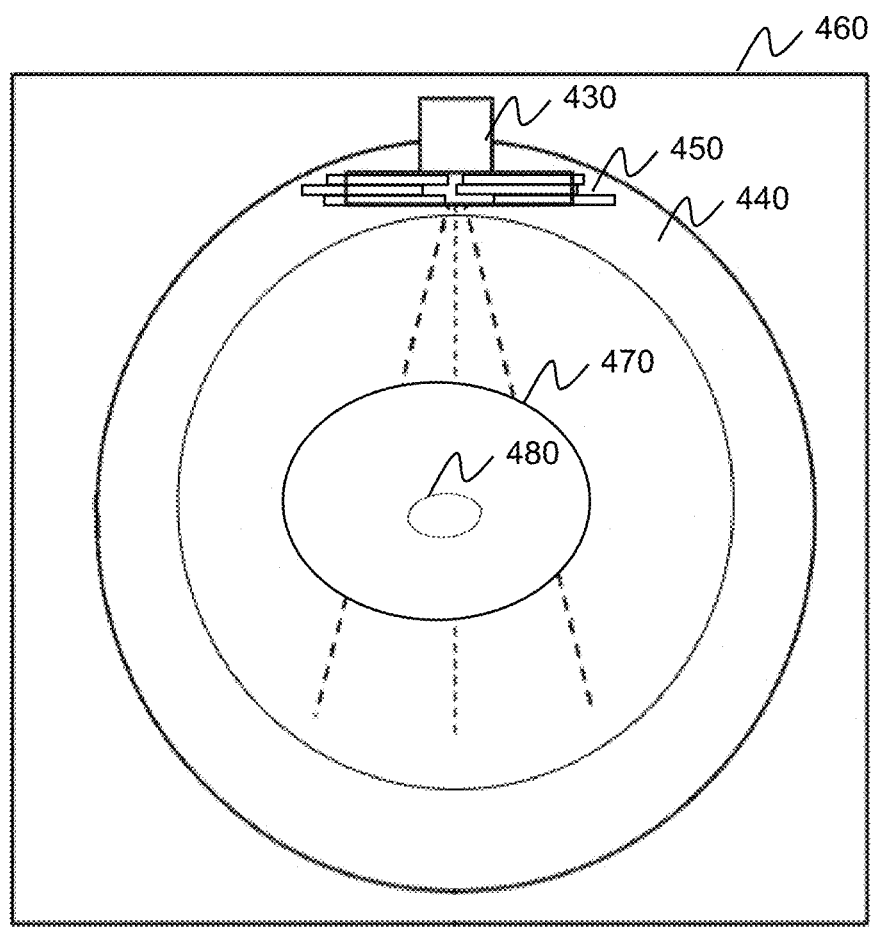

FIGS. 4A and 4B are schematic diagrams illustrating an exemplary radiation delivery device according to some embodiments of the present disclosure. FIGS. 4A and 4B may illustrate two exemplary configures of the radiation delivery device. In some embodiments, the radiation delivery device 400 may be an exemplary embodiment of the radiation delivery device 110 but shall not be considered as the only possible configuration of the radiation delivery device 110. People having ordinary skill in the art may, under the teaching of the present disclosure, add, delete, or amend any components in the radiation delivery device 110 or 400. Such amendment is also under the protection scope of the present application. Unless otherwise stated, components with the same names in the radiation delivery device 110 and the radiation delivery device 400 may have the same or similar functions.

As shown in FIG. 4A, the radiation delivery device 400 may include a treatment radiation source 430 (also referred to as a first radiation source), a multi-leaf collimator (MLC) 450, an imaging radiation source 410 (also referred to as a second radiation source), a radiation detector 420, a rotary ring 440, and a gantry 460. The imaging radiation source 410, the treatment radiation source 430, and the radiation detector 420 may be mounted on a rotary ring 440. An object 470 (e.g., a patient) may lie on a bed (not shown in the figure). The gantry 460 may be stationary or may be rotatable. The object 470 may include a treatment region 480 and be scanned and/or receive radiotherapy.

The imaging radiation source 410 may emit an imaging beam toward an imaging region of the object 470. The radiation detector 420 may receive an attenuated imaging beam that transmits through the imaging region, and generate image data associated with the imaging region. In some embodiments, the imaging radiation source 410 may be configured to emit an imaging beam to the object 470. The imaging beam may include a particle beam, a photon beam, or the like, or a combination thereof. The shape of the imaging beam may be a line, a narrow pencil, a narrow fan, a fan, a cone, a wedge, a tetrahedron, or the like, or a combination thereof. For example, the radiation source may be a cone beam computed tomography (CBCT) radiation source and the imaging beam may be a cone beam.

The radiation detector 420 may be configured to detect or receive radiation associated with at least a portion of the imaging beam emitted from the imaging radiation source 410 to generate imaging data (e.g., projection data). The imaging data may be transmitted to the processing device 140 for further processing. The processing device 140 may reconstruct an image of the object or a portion thereof based on the imaging data. The location of the treatment region 480 of the object 470 may be determined based on the image. In some embodiments, the radiation detector 420 may include one or more detector units. A detector unit may include a scintillator layer (e.g., a cesium iodide scintillator layer, a gadolinium oxysulfide scintillator layer), a gas detector, etc.

In some embodiments, the imaging radiation source 410 and the radiation detector 420 (which are also referred to an imaging assembly collectively) may be configured to provide image data for generating an image of the treatment region 480 (or an imaging region that overlaps with the treatment region 480), which may be used to determine a real-time location of the treatment region 480, and/or track the motion of the treatment region 480 during a radiotherapy operation performed by the treatment radiation source 430. In some embodiments, the location of the treatment region 480 of the object may change with time due to various motions, for example, cardiac motion (and its effect on other organs), respiratory motion (of the lungs and/or the diaphragm, and its effect on other organs), blood flow and motion induced by vascular pulsation, muscles contraction and relaxation, secretory activity of the pancreas, or the like, or a combination thereof. The location of the treatment region 480 may be monitored based on an image (e.g., a CT image, a cone beam computed tomography (CBCT) image, an MRI image, a PET image, a PET-CT image) of the object 470 generated according to the image data acquired by the imaging assembly before, during, and/or after the radiotherapy operation.

The treatment radiation source 430 may be configured to deliver a treatment beam toward a treatment region 480 of the object 470. For example, the process of delivering the treatment beam toward the treatment region 480 of the object may refer to a radiotherapy (RT). The treatment region 480 may include a cell mass, a tissue, an organ (e.g., a prostate, a lung, a brain, a spine, a liver, a pancreas, a breast, etc.), or a combination thereof. In some embodiments, the treatment region 480 may include a tumor, an organ with a tumor, or a tissue with a tumor. The treatment beam may include a particle beam, a photon beam, an ultrasound beam (e.g., a high intensity focused ultrasound beam), or the like, or a combination thereof. The particle beam may include a stream of neutrons, protons, electrons, heavy ions, or the like, or a combination thereof. The photon beam may include an X-ray beam, a γ-ray beam, an α-ray beam, a β-ray beam, an ultraviolet beam, a laser beam, or the like, or a combination thereof. The shape of the X-ray beam may be a line, a narrow pencil, a narrow fan, a fan, a cone, a wedge, or the like, or a combination thereof.

The MLC 450 may be disposed in a radiation path of the beam (e.g., the treatment beam, the imaging beam). The MLC 450 may be configured to further shape the beam and/or select a beamlet of the beam (i.e., a portion or component of the beam). In some embodiments, the MLC 450 may include a plurality of leaves. The plurality of leaves may form an aperture. The aperture may modify the shape of the beam. In some embodiments, one or more leaves of the MLC 450 may be moved during the rotation of the rotary ring 440 according to a treatment plan. The shape of the aperture may be changed according to a desired segment shape of the treatment plan. More descriptions of the desired shape may be found elsewhere in the present disclosure (e.g., FIG. 8, and the description thereof). More descriptions of the treatment plan may be found in PCT Application No. PCT/CN2018/085279 entitled "SYSTEMS AND METHODS FOR GENERATING RADIATION TREATMENT PLAN" filed May 2, 2018, the contents of which are hereby incorporated by reference.

FIG. 4B may illustrate another exemplary embodiment of the radiation delivery device 110 according to some embodiments of the present disclosure. As shown in FIG. 4B, the radiation delivery device 405 may include the treatment radiation source 430, the rotary ring 440, the MLC 450, and the gantry 460. The radiation delivery device 405 may be configured to perform radiotherapy. The radiation delivery device 405 may include a three dimensional conformal RT (3D-CRT) device, an intensity modulated RT (IMRT) device, an image-guided RT (IGRT) device, a biologically conformal RT (BCRT) device, or the like.

In some embodiments, as illustrated in FIGS. 4A and 4B, the gantry 460 or the rotary ring 440 may rotate at a relatively high speed (e.g., >60 rpm). In addition to increasing the rotation speed of the gantry 460 (or the rotary ring 440), the MLC 450 may also need to operate at a relatively high speed. In some embodiments, the leaf speed of MLC may be likely the limiting factor in contemporary therapy systems capable of fast gantry rotation (e.g., >2 rpm) and/or high radiation output rates (e.g., >300 MU/min). Therefore, it is desirable to develop an MLC configuration that has a relatively high speed to work in concert with the gantry 460 (or the rotary ring 440) configured to rotate at a high rotation speed. More descriptions of such an MLC configuration may be found elsewhere in the present disclosure (e.g., FIGS. 5-7B and the descriptions thereof).

Figure 5:
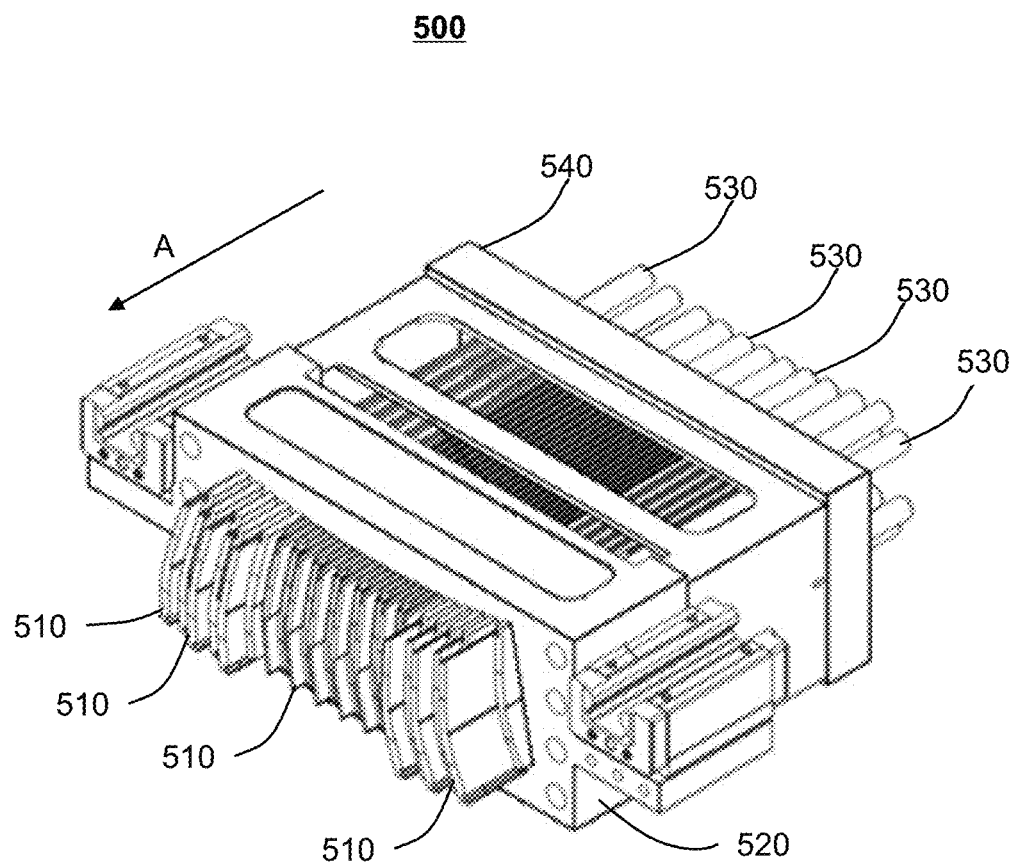
FIG. 5 is a schematic diagram illustrating an exemplary MLC according to some embodiments of the present disclosure.

FIG. 5 is a schematic diagram illustrating an exemplary MLC according to some embodiments of the present disclosure. As shown in FIG. 5, the MLC 500 may include a plurality of leaves 510, a rail box 540, one or more drive mechanisms 530, and a housing 520. In some embodiments, the housing 520 may be configured to accommodate the plurality of leaves 510, the drive mechanism(s) 530, etc. In some embodiments, the housing 520 may connect with the rail box 540.

In some embodiments, the plurality of leaves 510 may be movable along a plurality of rails disposed on the rail box 540. In some embodiments, at least some leaves 510 of the plurality of leaves may be movable in a direction parallel to each another. In some embodiments, at least some of the leaves 510 may be configured to move simultaneously while the radiation delivery is off. The plurality of leaves 510 may be configured to shield a portion of radiation beams and form an aperture to allow a portion of the radiation beams to pass through. The portion of the radiation beams passing through the aperture may reach the treatment region 480 to perform the radiation therapy. In some embodiments, the processing device 140 may control at least one leaf 510 of the MLC 500 to move into one or more positions to modify the shape of the aperture according to one or more parameters associated with the MLC 500 (e.g., a segment shape defined by the shape of the aperture formed by the MLC 500). The parameter(s) may be pre-determined by the processing device 140, or may be determined according to a specific condition. In some embodiments, the parameter(s) may be preset in the treatment plan.

The MLC 500 may include one or more leaves that can move continuously or assume discrete positions. In some embodiments, the MLC 500 may include one or more leaves that are "binary" in that the leaves may assume only closed (i.e., radiation-shielding) and open (i.e., radiation-transmitting) states. Such an MLC including "binary" leaves may be referred to as a binary MLC. In some embodiments, each leaf 510 may be configured to be movable between at least two positions. In some embodiments, one or more of the at least two positions may be adjustable. In some embodiments, the at least two positions may be determined or adjusted by the processing device 140. In some embodiments, each leaf 510 may have a closed position (or radiation-shielding position) and an open position (or radiation-transmitting position). If a leaf is at its closed position, the passage of a radiation beamlet of the radiation beam may be blocked. If a leaf is at its open position, the passage of a radiation beamlet of the radiation beam may be permitted. The leaves 510 at their corresponding open positions may form an aperture, such that the radiation beam (e.g., the treatment beam emitted from the treatment radiation source 430) may pass through the aperture, shaped by the MLC 500, and reach the object 470 to perform the RT. In some embodiments, the closed position and/or the open position of a leaf may be adjustable according to the treatment plan. For instance, a leaf may have multiple open positions that may define one or more aperture shapes.

The drive mechanism(s) 530 may be configured to actuate one or more of the leaves 510 to move. In some embodiments, the drive mechanism(s) 530 may facilitate the movement of the leaves 510 such that the MLC 500 can translate the leaves 510 between a first aperture shape and a second aperture shape. In some embodiments, each leaf 510 may be capable of translating between a first position and a second position (e.g., from an open position to a closed position, from a closed position to an open position). In some embodiments, each leaf 510 may be actuated to move independently or separately. In some embodiments, two or more leaves 510 may be actuated to move simultaneously. More descriptions of the configuration of each leaf may be found elsewhere in the present disclosure (e.g., FIGS. 6A-7B and descriptions thereof).

In some embodiments, the drive mechanism(s) 530 may include a fluid-power drive mechanism, a spring-based drive mechanism, an electric-charge-based drive mechanism, or the like, or a combination thereof. In some embodiments, the drive mechanism(s) 530 may include a plurality of driving motors. The fluid-power drive mechanism may include one or more fluid-power components, for example, a hydraulic or pneumatic driven piston in a cylinder. The cylinder may have one or more valves that may be independently controlled to regulate the flow and/or pressure of the fluid therein. An exemplary fluid-power drive mechanism may be a pneumatic drive mechanism. The pneumatic drive mechanism may actuate one or more leaves 510 to move by compressed gas loaded in the cylinder. The spring-based drive mechanism may actuate one or more leaves 510 to move by a loaded spring. The spring-based drive mechanism may include one or more springs that apply force(s) on one or more leaves 510 to translate between an open position and a closed position. For example, a leaf 510 may be coupled to a spring resonator that translates the leaf between the open position and the closed position. The electric-charge-based drive mechanism may actuate one or more leaves 510 to move by an electromagnetic motor or a piezoelectric motor. In some embodiments, a driving motor may actuate one or more leaves 510 to move. The drive mechanism(s) 530 may move each leaf of the MLC 500 individually and/or independently, or may move two or more leaves together.

In some embodiments, the MLC 500 may include 64 leaves, but it should be understood that the number of the leaves 510 in the MLC 500 may be varied, for example, 12, 15, 16, 24, 25, 31, 32, 36, 48, 50, 64, 72, 75, 100, 101, 120, 128, 135, etc. In some embodiments, each leaf 510 of the MLC 500 may have a width of about 1 mm to about 10 mm (e.g., about 2 mm). In some embodiments, the travel length of each leaf may be from about 0.25 cm to about 3 cm (e.g., about 1 cm). The smaller the travel range, the more precisely the radiation may be delivered. However, in some embodiments, reducing leaf travel length and/or width may prolong patient treatment time. The size and shape of the leaves 510 may be at least partially determined by the geometry of the gantry 460, the width of the radiation beam, and/or the desired "resolution" at which radiation is to be applied (e.g., leaf width, number of leaves). The depth of the leaves 510 may be sufficiently thick to impede the transmission of the radiation beam when the leaves 510 are in the closed position.

Alternatively or additionally, in some embodiments, each of the plurality of leaves 510 may include a support structure (not shown). The support structure may be configured to operably couple each of the plurality of leaves 510 with a drive mechanism 530 and/or other components of the MLC 500. The support structure may include a frame of beams, bars, rods, and/or brackets that may help to stabilize the leaves 510 in the vertical direction as they move in a horizontal direction. In some embodiments, the support structure may optionally include openings, hooks, notches, protrusions, grooves, or the like, or a combination thereof, so that a drive mechanism and/or another component (e.g., a stop block shown in FIGS. 6A-7B) may be attached to the leaf. In some embodiments, the support structure may comprise a truss framework. In some embodiments, the MLC 500 may include a plurality of leaf guides (not shown) that correspond with the leaves 510 to guide the movement of the leaves 510 along a path (e.g., a linear path). In some embodiments, the MLC 500 may include a plurality of stop blocks (see, e.g., FIGS. 6A-7B) corresponding to the plurality of leaves 510. Each stop block of the plurality of stop blocks may be configured to define a position of a corresponding leaf of the plurality of leaves 510. In some embodiments, each stop block may be movable, and the position(s) of a corresponding leaf may be adjustable by moving the each stop block. In some embodiments, each stop block may be moved by a driving mechanism (e.g., a driving motor) to one or more target positions to define the position(s) of the corresponding leaf. In some embodiments, the driving mechanism may move the stop block(s) when the radiation delivery is on.

In some embodiments, the speed of a leaf movement may be increased by increasing the speed of the drive mechanism(s) 530. Alternatively or additionally, the MLC 500 may optionally use reduced-weight leaves. In some embodiments, only a portion of the leaves 510 that shield the radiation beam may have a high-Z material (e.g., tungsten), while the peripheral support structure(s) of the leaves 510 may include lighter-weight materials. In some embodiments, a portion of a leaf 510 may be made of a substantially-radiation-impermeable material (e.g., tungsten), while the remaining portion of the leaf 510 may be made of one or more other materials (e.g., a material that is less dense and/or lighter than the substantially-radiation-impermeable material, such as stainless steel or titanium). In some embodiments, the portion of the leaf 510 made of a substantially-radiation-impermeable material may also be referred to as a substantially-radiation-impermeable portion of the leaf 510. In some embodiments, removing or hollowing out one or more regions of the leaf 510 may help to reduce the weight of the leaf 510 with little or no impact on the ability of the leaf 510 to impede radiation transmission. For example, a first section of the substantially-radiation-impermeable portion of the leaf 510 that is in the radiation path may be substantially solid, while a second section of the substantially-radiation-impermeable portion of the leaf 510 that is not in the radiation path may have one or more hollow regions.

In some embodiments, the MLC 500 may be designed for conformal therapy. In some embodiments, a large number of leaves 510 (e.g., 64 leaves, 120 leaves, etc.) can be adjusted in the longitudinal direction (as indicated by the arrow A) with a relatively high spatial resolution and precision, but with a limited speed. In some embodiments, for example, in volumetric arc therapy (VMAT), a binary MLC may be used. In some embodiments, a binary MLC may have a relatively high translation speed. In some embodiments, the relatively high translation speed may be provided by using a fast pneumatic actuation mechanism, which may offer a limited spatial resolution and/or precision and causes longer treatment times, especially for large tumors. For instance, to deliver radiation to a treatment region of the object 470 (e.g., a tumor) with a specific contour, a binary MLC (e.g., tomotherapy binary MLC) that is configured to provide a limited spatial resolution (e.g., the spatial resolution of a single slice of volume) may need to undergo multiple modulations in which different aperture shapes are formed to conform to the specific contour of the treatment region, thereby causing a long treatment time. In some embodiments, a continuous adjustment of the position(s) of the leaves 510 while at the same time modulating the dose rate to reduce the exposure to an undesired region of the object 470 may be used to match the tomotherapy performance of the radiation delivery device 400. The lack of a fast modulation of a conventional MLC can be countered in part by multiple passes of the radiation beams, but may still cause longer treatment times. A conventional MLC may have a plurality of leaf pairs, and the leaves may be generally driven by driving motors, which may offer a relatively high spatial resolution and precision. But the leaf speed of conventional MLC is limited, which may cause a slow modulation. For the convenience of dose modulation it is desirable to independently optimize the aperture shapes formed by the MLC 500 for each gantry angle or gantry angle segment. For this mode of operation, it is desirable to make the MLC 500 stationary while the radiation delivery is on, and then be switched quickly to a different shape while the radiation delivery is off, such that the MLC 500 may have a relatively high translation speed and a relatively high spatial resolution and precision. In this way, the duty cycle of the radiation delivery device 400 can be increased and the overall treatment time can be reduced. Because a conventional MLC actuated with motors and/or gears may offer a relatively limited translation speed (between two desired conformations) of the leaves but a relatively high spatial resolution, and the binary MLC can be actuated much faster, it is desirable to combine the advantages of a conventional MLC and those of a binary MLC. In some embodiments, the MLC 500 may be configured as a combination of the characteristics of a conventional MLC and a binary MLC. In some embodiments, each of one or more leaves of the MLC 500 may translate from one position to a next position fast while the radiation delivery is off, while the mechanism that defines the next position of each of the one or more leaves of the MLC 500 may be set in place when the radiation delivery is on. More descriptions of the configuration of the MLC 500 may be found elsewhere in the present disclosure (e.g., FIGS. 6A-7B and the descriptions thereof).

Figure 6A:
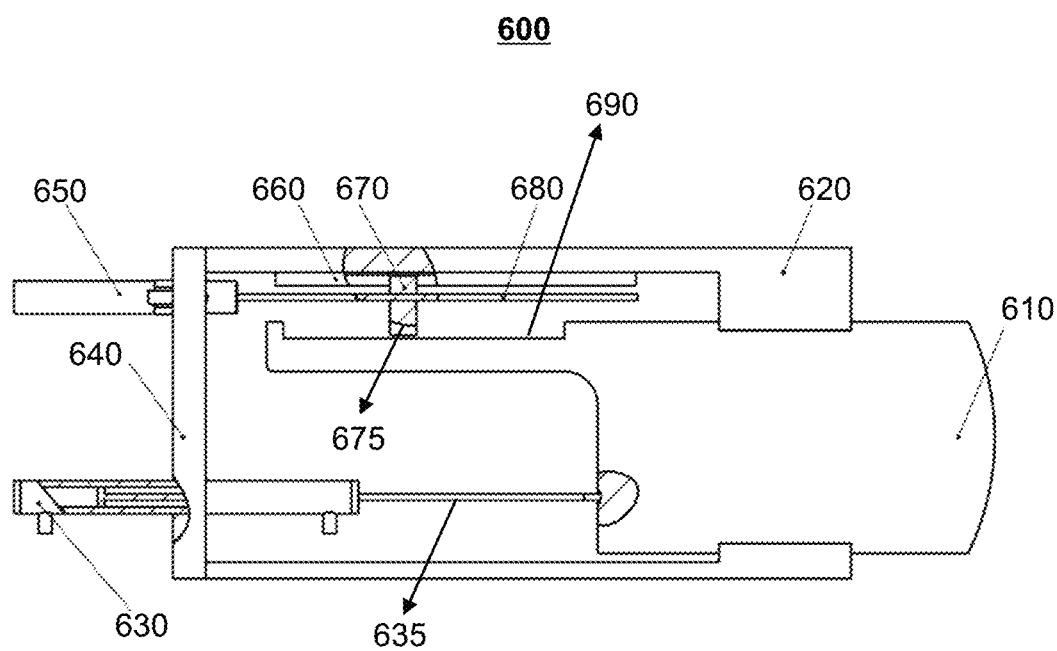
FIGS. 6A and 6B are schematic diagrams illustrating an exemplary leaf module of an MLC according to some embodiments of the present disclosure.
Figure 6B:
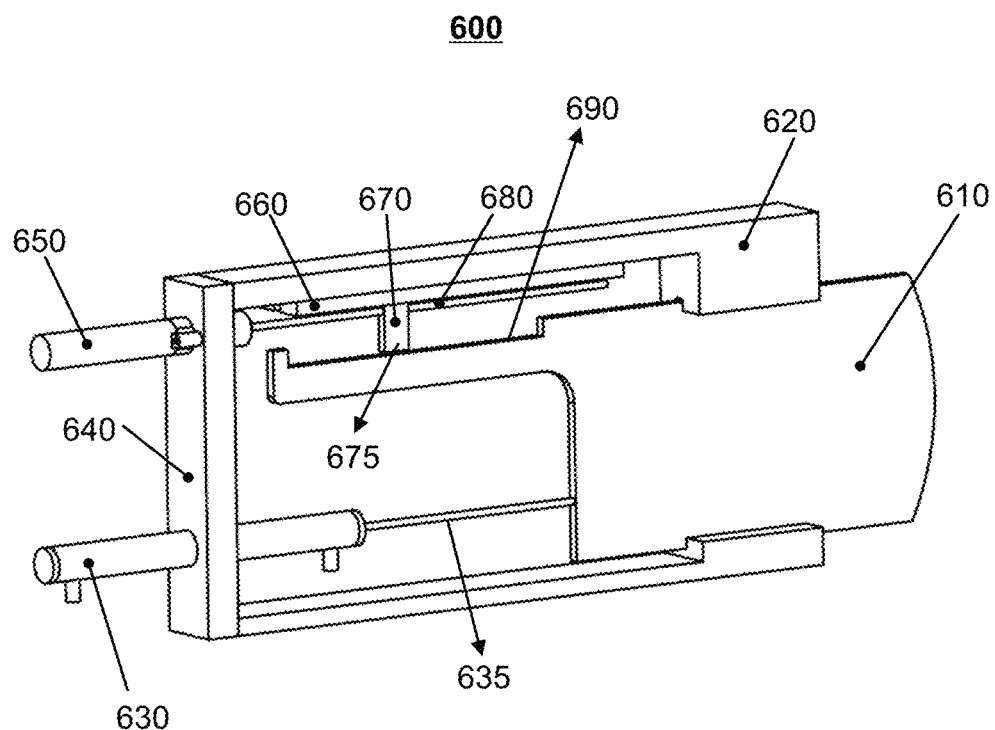

FIGS. 6A and 6B are schematic diagrams illustrating an exemplary leaf module of an MLC according to some embodiments of the present disclosure. FIG. 6A is a cross-sectional view of the leaf module 600. FIG. 6B is a perspective view of the leaf module 600. As shown in FIGS. 6A and 6B, the leaf module 600 may include a leaf 610, a leaf guide 620, and a first drive mechanism 630. The leaf 610 may be configured to shield a portion of radiation beams. In some embodiments, the leaf 610 may be made of a substantially-radiation-impermeable material. In some embodiments, in order to reduce the weight of the leaf 610, a first portion of the leaf 610 that is in the radiation path of the radiation beams when the leaf 610 is in the closed position may be made of a substantially-radiation-impermeable material, while the other portion of the leaf 610 may be made of one or more other materials that are less dense or lighter than the substantially-radiation-impermeable material. For example, the first portion of the leaf 610 may be made of tungsten, while the other portion of the leaf 610 may be made of a lighter material, such as stainless steel or titanium. In some embodiments, the leaf 610 may be configured to be movable between at least two positions (e.g., a closed position, an open position). In some embodiments, at least one of the at least two positions may be adjustable. For example, the leaf 610 may be moved quickly from a first position to a second position. The first position and/or the second position may be adjustable. In some embodiments, the leaf 610 may be configured to be movable between at least three positions. For instance, the leaf 610 may be configured to be movable between a closed position and an open position, in which the open position is adjustable; in other words, there are multiple open positions.

The leaf guide 620 may be configured to guide a movement of the leaf 610 such that the leaf 610 is capable of moving along the leaf guide 620. The first drive mechanism 630 may be configured to actuate a movement of the leaf 610 (e.g., from a first position to a second position). In some embodiments, the first drive mechanism 630 may be configured to actuate the leaf 610 to move at a first speed. In some embodiments, the leaf 610 may be connected to or coupled with the first drive mechanism 630 via a lever 635. In some embodiments, the first drive mechanism may include a pneumatic drive mechanism (e.g., a pneumatic cylinder), a spring-based mechanism (e.g., a loaded spring), an electric-charge-based mechanism (e.g., an electromagnetic motor, a piezoelectric motor), or the like, or any combination thereof. The pneumatic cylinder may have one or more valves that may be controlled to regulate the flow and/or pressure of a fluid (e.g., compressed gas) therein, which in turn may actuate the leaf 610 to move between the at least two positions. The loaded spring may apply force(s) onto the leaf 610 to translate between the at least two positions. The electric-charge-based mechanism may include an electromagnetic motor or a piezoelectric motor that is configured to actuate the leaf 610 to move between the at least two positions.

In some embodiments, the leaf module 600 may also include a second drive mechanism 650, a block guide 660, and a stop block 670. The second drive mechanism 650 may be configured to actuate the stop block 670 to move at a second speed. In some embodiments, the second speed may be lower than the first speed at which a leaf 610 moves. Using the second drive mechanism 650, the stop block 670 may be moved with relatively high precision. In some embodiments, the second drive mechanism 650 may include a driving motor. The driving motor may be connected with a spindle 680. The spindle 680 may transmit a driving force of the driving motor to the stop block 670, such that the stop block 670 can be moved and the position(s) of the stop block 670 can be adjusted. In some embodiments, the block guide 660 may be configured to guide a movement of the stop block 670. The stop block 670 may be configured to define the position(s) of the leaf 610.

In some embodiments, as shown in FIGS. 6A and 6B, a leaf 610 may include a notch 690 that sets on an edge of the leaf 610. In some embodiments, the stop block 670 may include a protruding part 675. The protruding part 675 may be configured to be operably coupled with the notch 690 of the leaf 610. In some embodiments, the protruding part 675 may be capable of extending into (or configured to extend into) the notch 690 of the leaf 610, such that the protruding part 675 of the stop block 670 restricts a movement of the leaf 610. In some embodiments, the notch 690 of the leaf 610 may be longer than the protruding part 675 of the stop block 670. Alternatively or additionally, the stop block 670 may include a notch that sets on an edge of the stop block, and the leaf 610 may include a protruding part. The protruding part of the leaf 610 may be configured to be operably coupled with the notch of the stop block 670. In some embodiments, the leaf 610 and the stop block 670 may also be uncoupled, such that the movement of the leaf 610 may not be affected or stopped by the stop block 670.

For example, the stop block 670 has a protruding part 675 and a leaf 610 has a notch 690 configured to operably couple the leaf 610 with the protruding part 675 of the stop block 670; the protruding part 675 of the stop block 670 may have two configurations, an extending configuration and a retracted configuration; when the protruding part 675 of the stop block 670 is in its extended configuration, the leaf 610 and the stop block 670 may be operably coupled; when the protruding part 675 of the stop block 670 is in its retracted configuration, the leaf 610 and the stop block 670 may be uncoupled. As another example, a leaf 610 has a protruding part and the stop block 670 has a notch configured to operably couple the stop block 670 with the protruding part of the leaf 610; the protruding part of the leaf 610 may have two configurations, an extending configuration and a retracted configuration; when the protruding part of the leaf 610 is in its extended configuration, the stop block 670 and the leaf 610 may be operably coupled; when the protruding part of the leaf 610 is in its retracted configuration, the stop block 670 and the leaf 610 may be uncoupled.

In some embodiments, the leaf 610 may be moved while the radiation delivery is off. The stop block 670 may be moved while the radiation delivery is on. In some embodiments, the leaf module 600 may include a brake component (not shown in FIGS. 6A and 6B). The brake component may be configured to keep a leaf 610 from moving when the stop block 670 is moving. In some embodiments, the brake component may be configured to keep one or more leaves of the MLC from moving when the stop blocks corresponding to the one or more leaves are moving. In some embodiments, the brake component may include a fastening structure, a blocking structure, or the like. More descriptions regarding the movement of the leaf 610 may be found elsewhere in the present disclosure (e.g., FIGS. 7A and 7B, and the descriptions thereof).

In some embodiments, the leaf module 600 may include one or more damp components (not shown in FIGS. 6A and 6B). In some embodiments, the damp component(s) may be set inside an inner chamber (not shown) of the leaf 610 and/or be coupled with the lever 635. The damp component(s) (also referred to as bumper(s) or damper(s)) may be configured to damp the motion of the leaf 610 at the end of a travel path of the leaf 610. Because the leaf 610 may be driven by the first drive mechanism 630 to move at a relatively high speed, excessive force of the first drive mechanism 630 and/or high repetition of the movement of the 610 may damage the lever 635 and/or a piston of the first drive mechanism 630 without damping. The damp component(s) may facilitate a relatively slow or gradual deceleration of the motion of the leaf 610 as it reaches the end of the travel path, which may help to prolong the life of the lever 635 and/or the piston.

In some embodiments, as shown in FIGS. 6A and 6B, the leaf module 600 may also include a base frame 640. The base frame 640 may be configured to support and/or connect one or more components of the leaf module 600 (e.g., the leaf 610, the leaf guide 620, the first drive mechanism 630, the second drive mechanism 650, the block guide 660, the stop block 670, and/or the spindle 680). In some embodiments, the base frame 640 may be made of one or more rigid materials.

It should be noted that the above descriptions of the leaf module 600 are merely provided for illustration purposes, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, at least a portion of the leaves in an MLC (e.g., the MLC 500 shown in FIG. 5) may be configured as the leaf module 600. In some embodiments, all leaves in the MLC (e.g., the MLC 500 shown in FIG. 5) may be actuated by one type of drive mechanism. For example, each leaf may be actuated by its corresponding pneumatic cylinder. Alternatively or additionally, at least two leaves in the MLC (e.g., the MLC 500 shown in FIG. 5) may be actuated by different types of drive mechanisms, respectively. For example, a first leaf may be actuated by a pneumatic cylinder, while a second leaf may be actuated by a loaded spring. In some embodiments, the leaf module 600 may include one or more other components, such as one or more shield components (e.g., the shield component 860 illustrated in FIGS. 8B and 8C). The shield component may be configured to shield one or more leaves 610 when the one or more leaves 610 are moving and/or the radiation delivery is on. Alternatively or additionally, the MLC (e.g., the MLC 500 shown in FIG. 5) may include a first portion of leaves 610, a second portion of leaves 610 (e.g., the remaining leaves of the MLC except for the first portion of leaves 610), and a shield component. The shield component may be configured to shield the first portion of the leaves 510 and/or the second portion of leaves. Merely by way of example, the first portion of the leaves 510 may be actuated to move and the second portion of the leaves 510 (e.g., the other leaves excluding the first portion) may be held still when the radiation delivery is on; the second portion of the leaves 510 are at their respective positions to allow passage of the radiation beams, and the first portion of the leaves 510 are shielded by the shield component. In some embodiments, the shield component may be capable of switching between a first shielding position where it shields the first portion of the leaves 510 and a second shielding position where it shields the second portion of the leaves 510. Using the shield component, at least a portion of the leaves 510 may be moved to next position(s) when the radiation delivery is on, and accordingly, the translation speed of the MLC 500 may be improved, and the duty cycle can be increased.

Figure 7A:
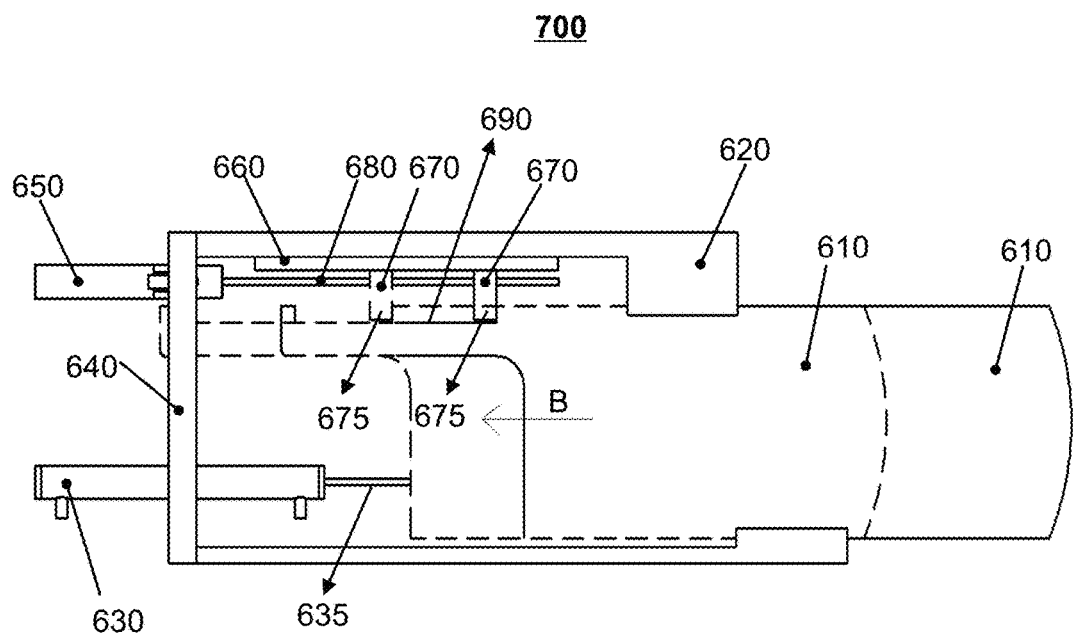
FIGS. 7A and 7B are schematic diagrams illustrating an exemplary leaf module translating between two different positions according to some embodiments of the present disclosure.
Figure 7B:
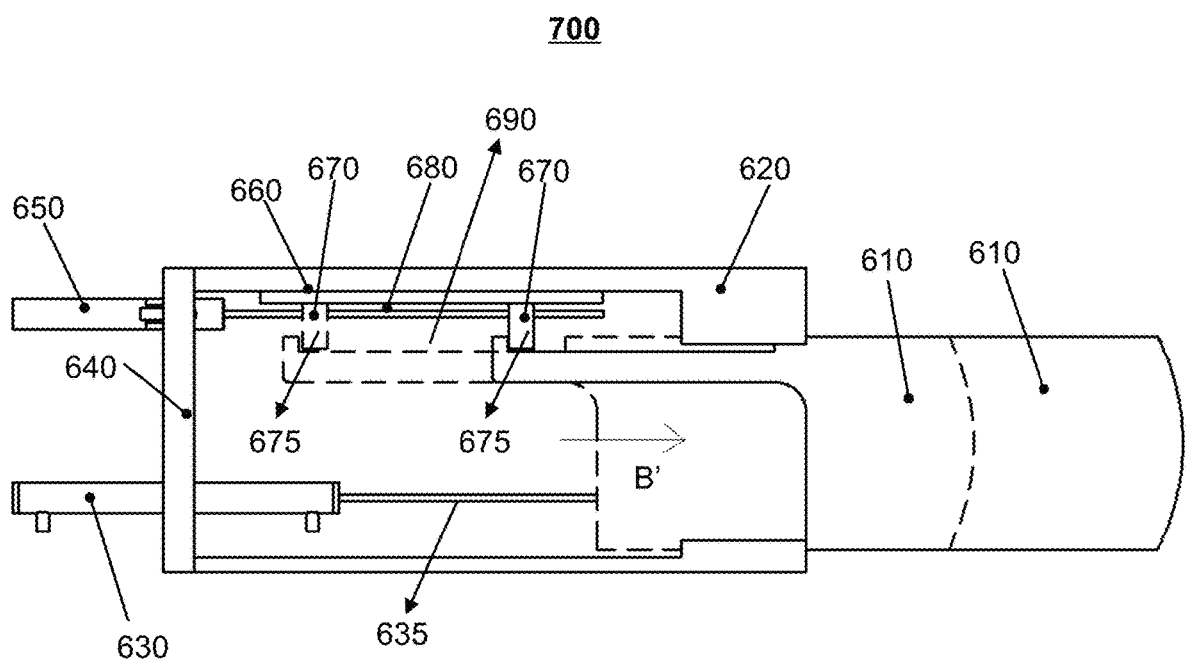

FIGS. 7A and 7B are schematic diagrams illustrating an exemplary leaf module translating between two different positions according to some embodiments of the present disclosure. As shown in FIGS. 7A and 7B, the leaf module 700 may include a leaf 610, a leaf guide 620, a first drive mechanism 630, a base frame 640, a second drive mechanism 650, a block guide 660, a stop block 670, and a spindle 680. In some embodiments, the leaf module 700 may be substantially the same as the leaf module 600 illustrated in FIGS. 6A and 6B. Unless otherwise stated, like reference numerals in the leaf module 600 and the leaf module 700 refer to like components having the same or similar functions. Thus, since the above components of the leaf module 700 have been described in connection with FIGS. 6A and 6B, the descriptions of which are not repeated herein.

FIG. 7A shows the movement of a leaf 610 in a first direction (e.g., from right to left) as indicated by the arrow B. As shown in FIG. 7A, before the leaf 610 is moved, the stop block 670 may be located at a first reference position (indicated by solid lines), and the leaf 610 may be restricted at a first target position (indicated by solid lines) by the stop block 670. The first target position of the leaf 610 may correspond to the first reference position of the stop block 670. The first target position of the leaf 610 may be defined by the first reference position of the stop block 670. Specifically, the right part of the notch 690 of the leaf 610 may be blocked by the stop block 670 (e.g., the protruding part 675 of the stop block 670), and thus, the leaf 610 cannot move to the left as indicated in FIG. 7A. In some embodiments, in order to move the leaf 610 to a second target position (indicated by dashed lines), the stop block 670 may be moved to a second reference position (indicated by dashed lines) corresponding to the second target position. The stop block 670 may be moved to the left along the block guide 660. In some embodiments, the stop block 670 may be actuated to move to the second reference position by the second drive mechanism 650 via the spindle 680 when the radiation delivery is on. In some embodiments, the leaf 610 may be kept from moving by a brake component (not shown) of the leaf 610 when the stop block 670 is moving. When the radiation delivery is off, the leaf 610 may be actuated to move to the second target position defined by the stop block 670. Specifically, the leaf 610 may be actuated by the first drive mechanism 630 to move along the leaf guide 620. For example, if the first drive mechanism 630 is a loaded spring, the force(s) on the loaded spring may be adjusted (e.g., becoming smaller) to pull the leaf 610. When the right part of the notch 690 of the leaf 610 is blocked by the stop block 670 (e.g., by the protruding part 675 of the stop block 670), the leaf 610 may stop at the second target position.

FIG. 7B shows the movement of a leaf 610 in a second direction (e.g., from left to right) as indicated by the arrow B'. As shown in FIG. 7B, before the leaf 610 is moved, the stop block 670 may be located at a first reference position (indicated by dashed lines), and the leaf 610 may be restricted at a first target position (indicated by dashed lines) by the stop block 670. The first target position of the leaf 610 may correspond to the first reference position of the stop block 670. The first target position of the leaf 610 may be defined by the first reference position of the stop block 670. Specifically, the left part of the notch 690 of the leaf 610 may be blocked by the stop block 670 (e.g., the protruding part 675 of the stop block 670), and thus, the leaf 610 cannot move to the right as indicated in FIG. 7B. In some embodiments, in order to move the leaf 610 to a second target position (indicated by solid lines), the stop block 670 may be moved to a second reference position (indicated by solid lines) corresponding to the second target position. The stop block 670 may be moved to the right along the block guide 660. In some embodiments, the stop block 670 may be actuated to move to the second reference position by the second drive mechanism 650 via the spindle 680 when the radiation delivery is on. In some embodiments, the leaf 610 may be kept from moving by a brake component (not shown) of the leaf 610 when the stop block 670 is moving. When the radiation delivery is off, the leaf 610 may be actuated to move to the second target position defined by the stop block 670. Specifically, the leaf 610 may be actuated by the first drive mechanism 630 to move along the leaf guide 620. For example, if the first drive mechanism 630 is a loaded spring, the force(s) on the loaded spring may be adjusted (e.g., becoming larger) to push the leaf 610. When the left part of the notch 690 of the leaf 610 is blocked by the stop block 670 (e.g., by the protruding part 675 of the stop block 670), the leaf 610 may stop at the second target position.

It should be noted that the above descriptions of the movement of the leaf module 700 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, the stop block 670 may be actuated to move to a plurality of reference positions, and the leaf 610 may be actuated to move to a plurality of target positions corresponding to the plurality of reference positions. In some embodiments, the position(s) of each leaf in an MLC (e.g., the MLC 500 as illustrated in FIG. 5) may be adjusted, at the same time or at different times, in a similar manner as the leaf module 700. In some embodiments, one or more leaves in an MLC (e.g., the MLC 500 as illustrated in FIG. 5) may be moved simultaneously while the radiation delivery is off. As illustrated in FIGS. 6A-7B, the stop blocks can be moved to next reference position(s) with a relatively high precision while the radiation delivery is on, and the leaves can be moved very quickly to next position(s) corresponding to or defined by the next reference position(s) of the stop blocks while the radiation delivery is off. Therefore, the translation speed of the MLC 500 may be improved, the duty cycle can be increased, and the spatial resolution of the aperture shape formed by the MLC 500 may be improved. In some embodiments, the leaves of the leaf module 600 or 700 may be shielded by a shield component so that the stop blocks and the leaves of the leaf module 600 or 700 may both be actuated to move to their respective desired positions while the radiation delivery is on; by this way, the leaves may be properly situated to form an aperture for radiation when the shield component is removed.

Figure 8A:
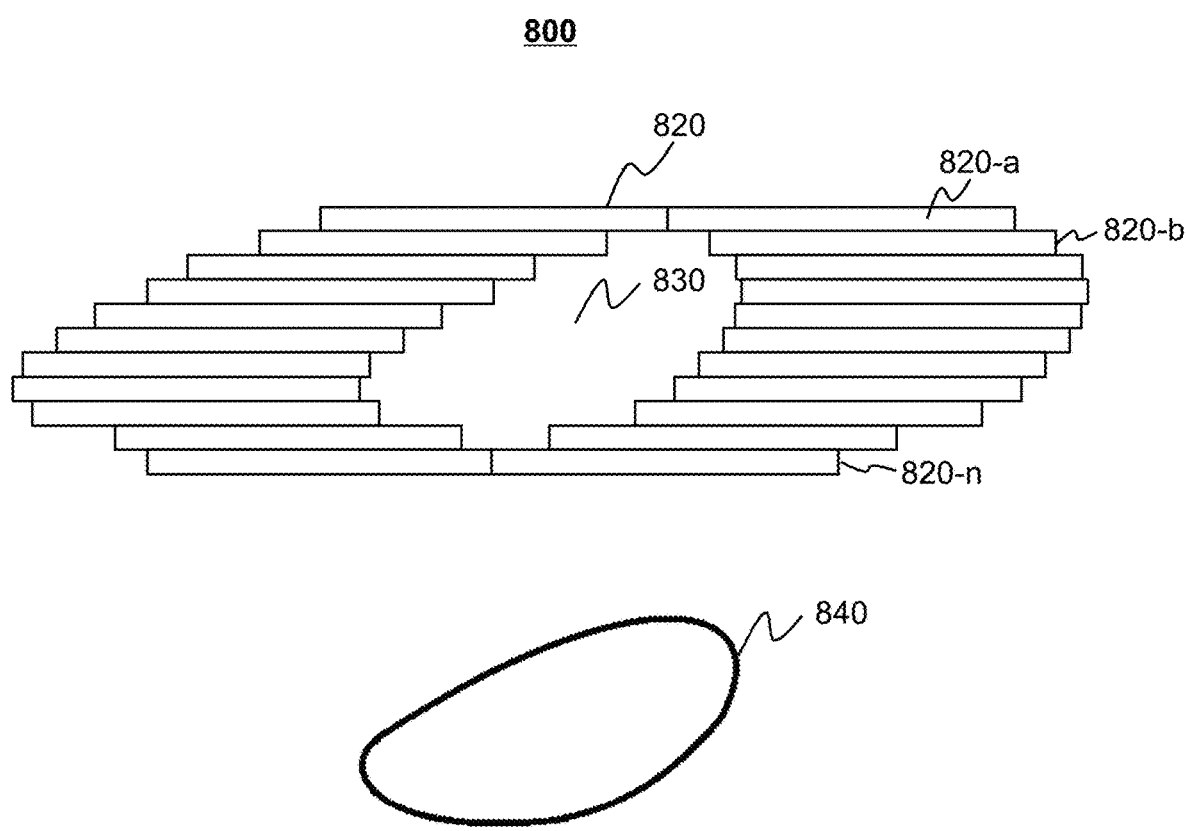
FIGS. 8A-8C are schematic diagrams illustrating exemplary aperture shapes formed by an MLC and a corresponding treatment region according to some embodiments of the present disclosure.
Figure 8B:
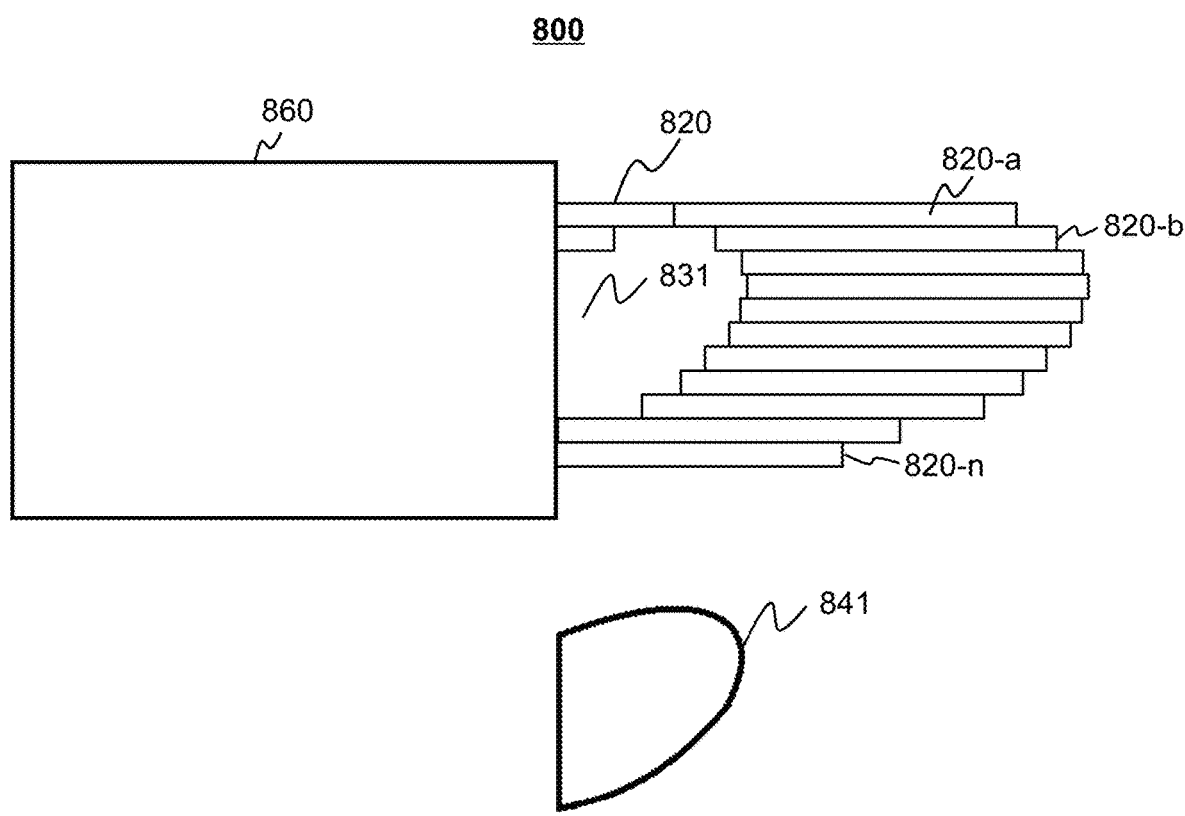
Figure 8C:
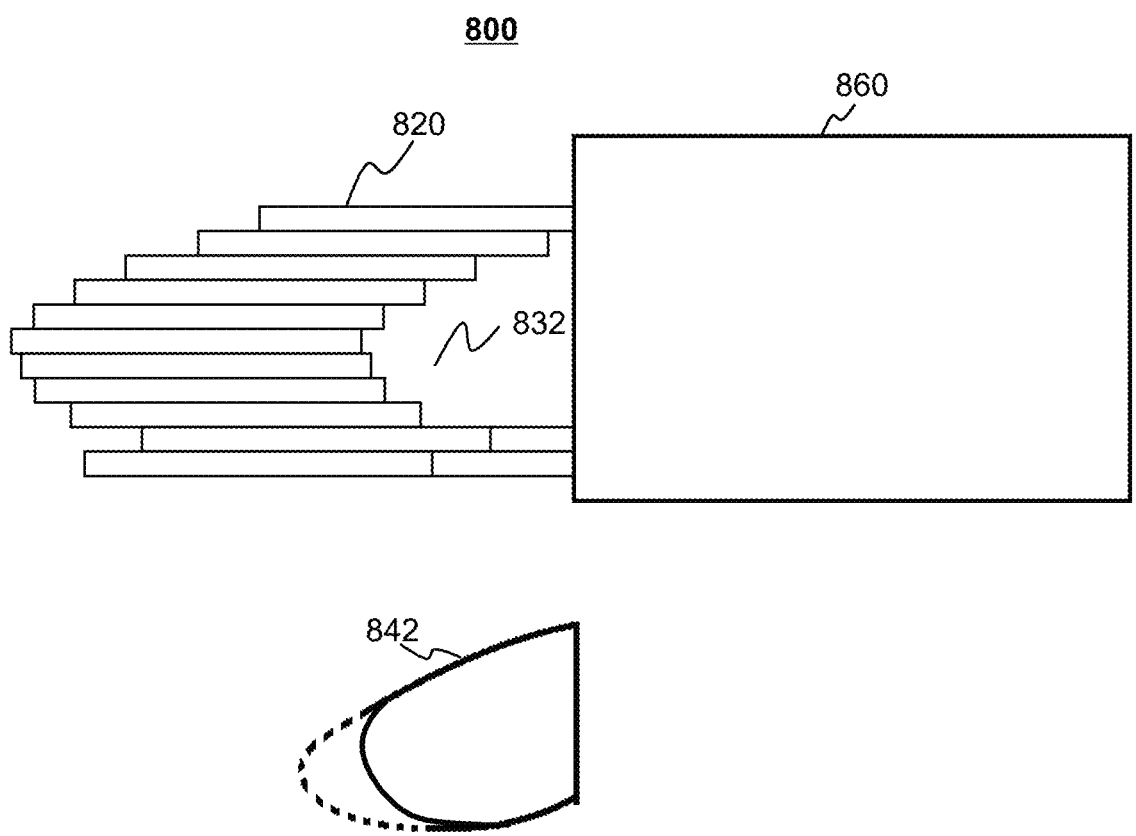

FIGS. 8A-8C are schematic diagrams illustrating exemplary aperture shapes formed by an MLC and a corresponding treatment region according to some embodiments of the present disclosure. In some embodiments, the MLC 800 may be placed between a treatment radiation source (e.g., the first radiation source 113, the treatment radiation source 430) and a bore (e.g., the bore 117). The MLC 800 may modify the shape of the radiation beam(s) emitted from the radiation source to a shape similar to the aperture 830 formed by the leaves 820 of the MLC. In some embodiments, the processing device 140 may obtain a treatment plan. The treatment plan may include a desired segment shape of a radiation segment. The desired segment shape may correspond to the shape of a desired treatment region 840.

As shown in FIG. 8A, the leaves 820 may include a plurality of leaf pairs, for example, 820-*a*, 820-*b*, . . . , 820-*n*. The plurality of leaf pairs may be arranged parallelly and moved to form the aperture 830 in order to deliver the treatment plan. The modified beam shape may correspond (or approximately correspond) to the desired treatment region 840 and be delivered toward the desired treatment region 840. A conformability of the MLC 800 may be determined based on the width of each leaf. The conformability of the MLC may indicate a similarity degree between the shape of the aperture 830 and a desired segment shape corresponding to the shape of the desired treatment region 840. A higher conformability may indicate that the shape of the aperture 830 is more similar to the desired segment shape corresponding to the shape of the desired treatment region 840. A higher conformability of the MLC 800 may be achieved by increasing the number (or count) of the leaves 820, reducing the width of each leaf of the MLC 800, etc. In some embodiments, each leaf of the MLC 800 may use the same or similar configuration as the leaf module 600 or the leaf module 700. That is, each leaf 820 may be movable between two or more positions, and the movement of the each leaf 820 may be apparently continuous, which may allow fine tune of the shape of the aperture 830 and in turn improve the spatial resolution of radiation treatment.

As shown in FIG. 8B, a shield component 860 may shield a first portion of the leaves 820 and form an aperture 831. The first portion of the leaves 820 may be actuated to move and the second portion of the leaves 510 (e.g., the other leaves excluding the first portion) may be held still when the radiation delivery is on; the second portion of the leaves 820 are at their respective positions to allow passage of the radiation beams, and the first portion of the leaves 820 are shielded by the shield component 860. The modified beam shape may correspond (or approximately correspond) to a desired treatment region 841 and be delivered toward the desired treatment region 841. In some embodiments, as shown in FIG. 8C, the shield component 860 may switch from a first shielding position where it shields the first portion of the leaves 820 to a second shielding position where it shields the second portion of the leaves 820, and an aperture 832 may be formed. The modified beam shape may correspond (or approximately correspond) to a desired treatment region 842 (see the solid lines in FIG. 8C) and be delivered toward the desired treatment region 842. The dashed lines illustrates an edge of the treatment region formed before the first portion of the leaves 820 are moved. Using the shield component 860, at least a portion of the leaves 820 may be moved to next position(s) when the radiation delivery is on, and accordingly, the translation speed of the MLC 800 may be improved, and the duty cycle can be increased. In some embodiments, the shield component 860 may be configured as a sheet or plate. In some embodiments, the shield component 860 may be made of a substantially-radiation-impermeable material that can block radiation. In some embodiments, the shield component 860 may be positioned in a plane perpendicular to the depth of the leaves 820. In some embodiments, the shield component 860 may have a shape of a rectangle, square, ellipse, round, polygon, or the like, or any arbitrary shape.

Figure 9:
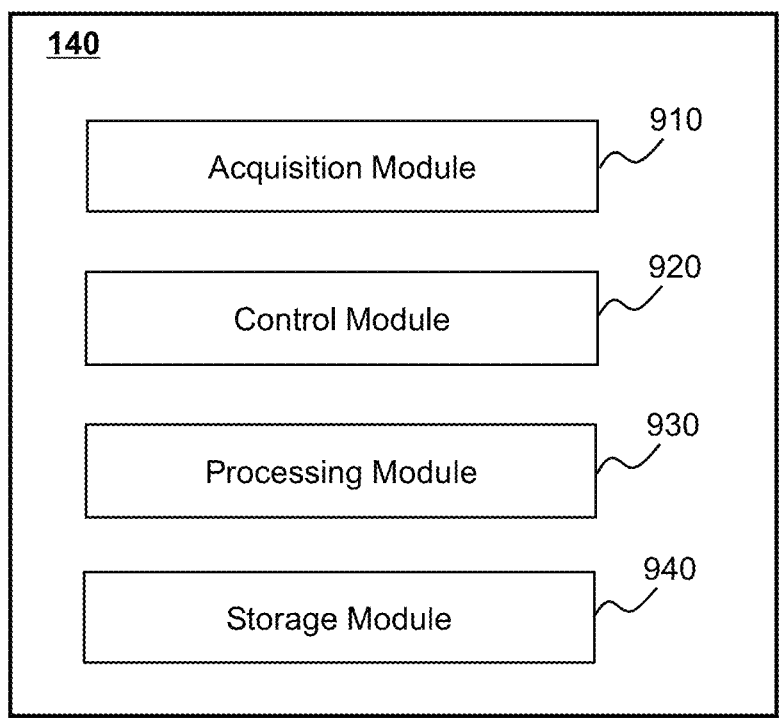
FIG. 9 is a block diagram illustrating an exemplary processing device according to some embodiments of the present disclosure.

FIG. 9 is a block diagram illustrating an exemplary processing device 140 according to some embodiments of the present disclosure. The processing device 140 may include an acquisition module 910, a control module 920, a processing module 930, and a storage module 940. At least a portion of the processing device 140 may be implemented on a computing device as illustrated in FIG. 2 or a mobile device as illustrated in FIG. 3.

The acquisition module 910 may be configured to acquire imaging data. In some embodiments, the acquisition module 910 may acquire the imaging data (e.g., CT imaging data) from the radiation delivery device 110, the terminal 130, the storage device 150, and/or an external data source (not shown). In some embodiments, the imaging data may include raw data (e.g., projection data). For example, the imaging data (e.g., projection data) may be generated based on detected imaging beams at least some of which have passed through an object being imaged and treated in the radiation delivery device 110. In some embodiments, the acquisition module 910 may acquire one or more instructions for processing the imaging data. The instructions may be executed by the processor(s) of the processing device 140 to perform exemplary operations described in this disclosure. In some embodiments, the acquired imaging data may be transmitted to the storage module 940 to be stored.

In some embodiments, the acquisition module 910 may acquire a treatment plan for an object. The treatment plan may include parameters associated with at least one radiation segments. For example, the radiation segment may be an arc-shaped segment on the rotation trajectory of the rotary ring at which the treatment radiation source delivers the treatment beam to the treatment region. As another example, the treatment plan associated with the MLC may include the desired segment shape corresponding to the shape of the desired treatment region 840. The acquisition module 910 may acquire the treatment plan from one or more components of the radiation system 100 (e.g., the storage device 150, the terminal 130), or from an external source (e.g., an electronic medical record, a medical database) via the network 120.

The control module 920 may control operations of the acquisition module 910, the storage module 940, the processing module 930 (e.g., by generating one or more control parameters), the radiation delivery device 110, or the like, or a combination thereof. For example, the control module 920 may cause the acquisition module 910 to acquire imaging data, the timing of the acquisition of the imaging data, etc. As another example, the control module 920 may cause the processing module 930 to process imaging data acquired by the acquisition module 910. In some embodiments, the control module 920 may control the operation of the radiation delivery device 110. For example, the control module 920 may cause the radiation delivery device 110 to start, pause, stop, and/or resume the delivery of the imaging beam and/or the treatment beam to the object. As another example, the control module 920 may cause the radiation delivery device 110 to adjust the radiation dose of the imaging beam or treatment beam to the object.

In some embodiments, the control module 920 may control components of the MLC (e.g., the MLC 500 in FIG. 5) according to the data acquired by the acquisition module 910, the data processed by the processing module 930 and/or parameters stored in the storage module 940. For example, the control module 920 may control (or cause) the radiation delivery to be on/off, control (or cause) a drive mechanism to actuate a stop block to move to a reference position corresponding to a target position of a leaf, and/or control (or cause) the leaf to move to the target position. As another example, the control module 920 may control (or cause) a brake component of the MLC to keep the leaf from moving when the stop block is moving. As a further example, the control module 920 may switch a shield component of the MLC to shield or expose the leaf. The control module 920 may perform or control one or more components of the radiation delivery device 110 to perform operation(s) illustrated in FIGS. 10 and 11.

In some embodiments, the control module 920 may receive a real-time instruction from an operator or retrieve a predetermined instruction provided by a user (e.g., a doctor) to control one or more operations of the radiation delivery device 110, the acquisition module 910, and/or the processing module 930. For example, the control module 920 may adjust the acquisition module 910 and/or the processing module 930 to generate one or more images of an object according to the real-time instruction and/or the predetermined instruction. As another example, the control module 920 may cause the radiation delivery device 110 to adjust the treatment beam delivered to the object according to the real-time instruction and/or the predetermined instruction. As a further example, the control module 920 may gate and/or adjust the delivery of the treatment beam based on real-time monitoring of the location of the treatment region of the object according to the generated image(s). As still a further example, the control module 920 may cause the position of the bed 115 and/or the first radiation source 113 to be adjusted according to the generated image(s), so that the treatment beam may target the treatment region of the object. In some embodiments, the control module 920 may communicate with one or more other modules of the processing device 140 for exchanging information and/or data.

The processing module 930 may process information provided by various modules of the processing device 140. The processing module 930 may process imaging data acquired by the acquisition module 910, imaging data retrieved from the storage module 940 and/or the storage device 150, etc. In some embodiments, the processing module 930 may reconstruct one or more images based on the imaging data according to a reconstruction technique. The reconstruction technique may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or a combination thereof. The reconstruction technique may be applied over a limited angular range to perform tomosynthesis imaging. In some embodiments, the processing module 930 may perform pre-processing on the imaging data before the reconstruction. The pre-processing may include, for example, imaging data normalization, imaging data smoothing, imaging data suppressing, imaging data encoding (or decoding), denoising, etc.

In some embodiments, based on one or more reconstructed images of an object including a treatment region, the processing module 930 may determine a change of location or shape of the treatment region due to, e.g., respiratory motion, cardiac motion, muscle contraction and relaxation, shrinkage or expansion of a lesion (e.g., a tumor) corresponding to the treatment region, etc. In some embodiments, the processing module 930 may determine, based on the images and the analysis thereof, whether any change or adjustment is needed with respect to the treatment plan, and/or determine the needed adjustment. According to the determined adjustment, the control module 920 may cause the adjustment to be implemented. For instance, the control module 920 may cause the radiation delivery device 110 to deliver an adjusted treatment beam or adjust a position of the object, and control (or cause) the MLC to adjust the shape of the aperture 830 formed by the leaves 820 of the MLC. For example, the processing module 930 may transmit the motion information of the treatment region to the control module 920. The control module 920 may accordingly control (or cause) the radiation delivery device 110 to adjust the delivery of the treatment beam by, for example, pausing the delivery and/or changing the position of the source of the treatment beam. As another example, the control module 920 may accordingly control (or cause) the radiation delivery device 110 to adjust the position of the object with respect to the treatment beam.

The storage module 940 may store imaging data, control parameters, processed imaging data, treatment plan, adjusted treatment plan, or the like, or a combination thereof. In some embodiments, the storage module 940 may store one or more programs and/or instructions that may be executed by the processor(s) of the processing device 140 to perform exemplary operations described in this disclosure. For example, the storage module 940 may store program(s) and/or instruction(s) that can be executed by the processor(s) of the processing device 140 to acquire imaging data of an object, reconstruct one or more images based on the imaging data, determine an ROI in the image(s), detect a change of location or shape of a treatment region of the object based on the image(s), revise the delivery of the treatment beam to the treatment region, and/or adjust the position of the object relative to the treatment beam based on the detected change of location or shape of the treatment region.

In some embodiments, one or more modules illustrated in FIG. 9 may be implemented in at least part of the radiation system 100 as illustrated in FIG. 1. For example, the acquisition module 910, the control module 920, the processing module 930, and/or the storage module 940 may be implemented via the processing device 140 and/or the terminal 130.

FIG. 10 is a flowchart illustrating an exemplary process for moving a leaf according to some embodiments of the present disclosure. In some embodiments, a stop block may be moved to a first reference position when radiation delivery is on, and then a leaf corresponding to the stop block may be moved to a first target position defined by the first reference position when the radiation delivery is off. In some embodiments, one or more operations of process 1000 illustrated in FIG. 10 may be performed by the processing device 140 (e.g., the control module 920). In some embodiments, one or more operations of process 1000 may be implemented in the radiation system 100 illustrated in FIG. 1. For example, the process 1000 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 9, or the like). As another example, a portion of the process 1000 may be implemented on the radiation delivery device 110. The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In some embodiments, the control module 920 may control (or cause) at least one leaf of an MLC (e.g., the MLC 500 as illustrated in FIG. 5) to move into one or more positions. In some embodiments, the control module 920 may control the at least one leaf of the MLC to move simultaneously while the radiation delivery is off. In some embodiments, the process to control (or cause) a leaf (e.g., the leaf 610, the leaf 820) of the at least one leaf to move to a first target position of the one or more positions may be achieved according to the following one or more operations. It is understood that the movement of multiple leaves of the MLC may be achieved and/or controlled similarly.

In 1010, the control module 920 may control (or cause) a second drive mechanism (e.g., the second drive mechanism 650) to actuate a stop block (e.g., the stop block 670) of the MLC to move to a first reference position corresponding to the first target position when the radiation delivery is on. The stop block may be configured to define a position of the leaf (e.g., the leaf 610). The stop block may be movable. In some embodiments, one or more target positions of the leaf may be adjusted through the movement of the stop block. In some embodiments, the second drive mechanism may include a driving motor. The driving motor may be configured to actuate the stop block to move to the first reference position when the radiation delivery is on. The first reference position may be used to define the first target position of the leaf.

In 1020, the control module 920 may control (or cause) a brake component of the MLC to keep the leaf (e.g., the leaf 610) from moving when the stop block is moving. When the stop block is moving, the radiation delivery may be on. In order to shield undesired radiation, the leaf needs to be held still when the radiation delivery is on.

In 1030, the control module 920 may control (or cause) a first drive mechanism (e.g., the first drive mechanism 630) to actuate the leaf to move to the first target position when the radiation delivery is off. When the radiation delivery is off, the leaf may be quickly moved to the first target position. In some embodiments, the first drive mechanism may include a pneumatic drive mechanism (e.g., a pneumatic cylinder), a spring-based drive mechanism (e.g., a loaded spring), an electric-charge-based mechanism (e.g., an electromagnetic motor, a piezoelectric motor), or the like, or any combination thereof. For example, the movement of the leaf to the first target position may be actuated by compressed gas. As another example, the movement of the leaf to the first target position may be actuated by a loaded spring. As a further example, the movement of the leaf to the first target position may be actuated by an electromagnetic motor or a piezoelectric motor.

In some embodiments of the present disclosure, when the radiation delivery is on, the stop block may be actuated by the second drive mechanism to move to a reference position by the driving motor, and the leaf may be held still. When the radiation delivery is off, the leaf may be actuated by the first drive mechanism to move quickly until the leaf is blocked by the stop block, and the leaf may stop at a target position (defined by the reference position). In some embodiments, the leaf may be moved at a first speed, and the stop block may be moved at a second speed lower than the first speed so that the reference position may have relatively high precision. Thus, the duty cycle of the radiation delivery device may be increased and the overall treatment time may be reduced.

It should be noted that the above descriptions of the process 1000 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, at least one of the leaves in the MLC may be moved according to process 1000. In some embodiments, two or more leaves of the MLC may be moved according to the process 1000 synchronously or alternately. In some embodiments, the process 1000 may be repeated to determine one or more target positions of the leaf.

Figure 11:
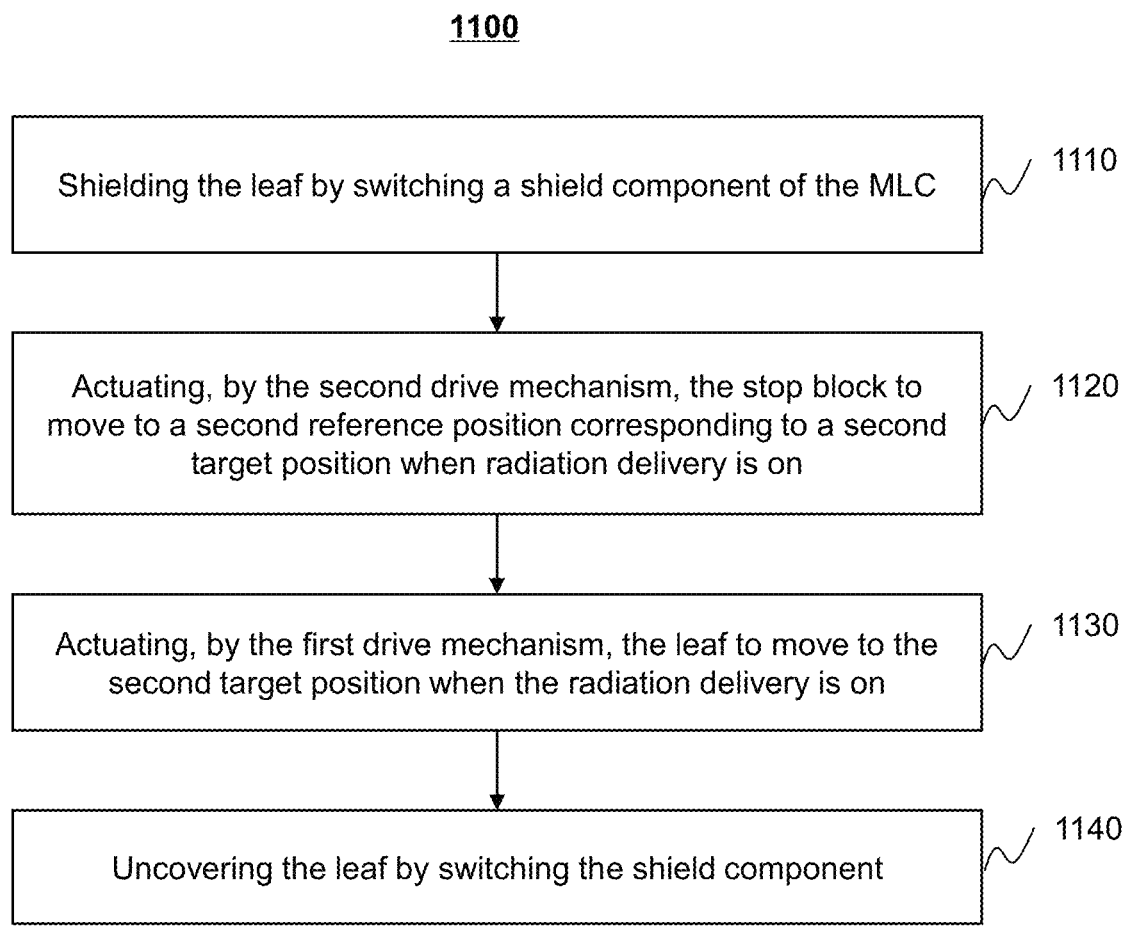
FIG. 11 is a flowchart illustrating another exemplary process for moving a leaf according to some embodiments of the present disclosure.

FIG. 11 is a flowchart illustrating another exemplary process for moving a leaf according to some embodiments of the present disclosure. In some embodiments, a leaf may be shielded by a shield component, a stop block may be moved to a second reference position when radiation delivery is on, and subsequently a leaf corresponding to the stop block may be also moved to a second target position corresponding to the second reference position when the radiation delivery is on, and then the leaf may be uncovered by removing the shield component to allow the passage of radiation beams through the leaf. In some embodiments, one or more operations of process 1100 illustrated in FIG. 11 may be performed by the processing device 140 (e.g., the control module 920). In some embodiments, one or more operations of process 1100 may be implemented in the radiation system 100 illustrated in FIG. 1. For example, the process 1100 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 9, or the like). As another example, a portion of the process 1100 may be implemented on the radiation delivery device 110. The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting.

In some embodiments, the control module 920 may control (or cause) at least one leaf of an MLC (e.g., the MLC 500 as illustrated in FIG. 5) to move into one or more positions. In some embodiments, the control module 920 may control (or cause) the at least one leaf of the MLC to move simultaneously while the radiation delivery is off. In some embodiments, the MLC may include a shield component configured to shield at least a portion of the leaves of the MLC. The coordination of such various components may facilitate radiation delivery in various manners according to treatment plans.

Merely by way of example, according to a specific treatment plan, in a first radiation segment, a specific portion of the subject may need no radiation, while in a second radiation segment, the specific portion of the subject may need to be exposed to radiation. To this end, in the first radiation segment, one or more leaves may be shielded by the shield component such that radiation is shielded from the specific portion of the subject as desired, and at least one of the one or more leaves may be adjusted to target position(s); in the second radiation segment, the one or more leaves may be exposed by switching the shield component away from the one or more leaves such that radiation may reach the specific portion of the subject as desired.

As another example, according to a specific treatment plan, in a first radiation segment, a first portion of the leaves may be shielded (by the shield component) but moved to their respective target positions, a second portion of the leaves may be at their respective open positions to form a first aperture, and the first segment shape may be achieved. In a second radiation segment following the first radiation segment, because the first portion of leaves are ready, the second segment of radiation delivery may be performed right after the first segment of radiation delivery is finished, which may save time. In the second radiation segment, the second portion of leaves may be shielded and moved to their respective target positions.

In some embodiments, a leaf of the one or more leaves may be moved to a target position according to the following one or more operations. It is understood that the movement of multiple leaves of the MLC may be achieved and/or controlled similarly.

In 1110, the control module 920 may control (or cause) a shield component of the MLC to be positioned or situated such that the leaf (e.g., the leaf 610) to be shielded by the shield component. In some embodiments, the shield component may be made of one or more substantially-radiation-impermeable materials that can block radiation. In some embodiments, when a portion of the subject does not need radiation within a radiation segment, the control module 920 may control (or cause) the shield component to shield the leaf.

In 1120, the control module 920 may control (or cause) the second drive mechanism to actuate the stop block (e.g., the stop block 670) to move to a second reference position corresponding to a second target position when the radiation delivery is on. The stop block may be configured to define a position of the leaf (e.g., the leaf 610). The stop block may be movable. One or more target positions of the leaf may be adjusted through the movement of the stop block. In some embodiments, the second drive mechanism may include a driving motor. The driving motor may actuate the stop block to move to the second reference position when the radiation delivery is on. The second reference position may be used to define the second target position of the leaf.

In 1130, the control module 920 may control (or cause) the first drive mechanism to actuate the leaf to move to the second target position when the radiation delivery is on. Because the leaf is shielded by the shield component (e.g., in the first radiation segment), the leaf may be quickly moved to the second target position when the radiation delivery is on, while the segment shape may be unaffected. In some embodiments, the first drive mechanism may include a pneumatic drive mechanism (e.g., a pneumatic cylinder), a spring-based drive mechanism (e.g., a loaded spring), an electric-charge-based mechanism (e.g., an electromagnetic motor, a piezoelectric motor), or the like, or any combination thereof. For example, the movement of the leaf to the second target position may be actuated by compressed gas. As another example, the movement of the leaf to the second target position may be actuated by a loaded spring. As a further example, the movement of the leaf to the second target position may be actuated by an electromagnetic motor or a piezoelectric motor.

In 1140, the control module 920 may control (or cause) the leaf to be exposed by switching the shield component away from the leaf (e.g., before the second radiation segment). After the leaf is moved to the second target position, the control module 920 may switch the shield component to expose the leaf. In this way, the radiation interval between the first radiation segment and the second radiation segment may be reduced, and the duty cycle may be increased.

It should be noted that the above descriptions of the process 1100 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, one or more operations may be added. For example, when the stop block is moving, the leaf may be kept from moving by a brake component. In some embodiments, the shield component may be configured to shield a first portion of the leaves or a second portion of the leaves. The shield component may be capable of switching from shielding the first portion of the leaves to shielding the second portion of the leaves, or from shielding the second portion of the leaves to shielding the first portion of the leaves.

In some embodiments, the MLC 500 may include a plurality of pairs of leaves configured to shield radiation beams. In some embodiments, the MLC 500 may include an actuator configured to drive at least one leaf of the plurality of pairs of leaves to translate among a first set of predefined positions at a first speed. In some embodiments, the MLC 500 may include a positioner non-synchronically movable along with the actuator among a second set of predefined positions at a second speed slower than the first speed. The positioner may be configured to place the at least one leaf at each of the first set of predefined positions. In some embodiments, the MLC 500 may include a position holder releasably coupled with the at least one leaf. The position holder may be configured to maintain the at least one leaf at the each of the first set of predefined positions when the positioner is moving from a first predefined position of the second set of predefined positions to a second predefined position of the second set of predefined positions. In some embodiments, the positioner may include a motor configured to drive the positioner to move at the second speed. In some embodiments, the actuator may refer to the first drive mechanism illustrated in FIGS. 6A-7B, 10, and 11. In some embodiments, the positioner may refer to the stop block illustrated in FIGS. 5-7B and 9-11. In some embodiments, the position holder may refer to the brake component illustrated in FIGS. 6A-7B and 9-11. In some embodiments, the first set of predefined positions and/or the second set of predefined positions may be predefined according to one or more treatment plans.

In some embodiments, the MLC 500 may include a plurality of pairs of leaves configured to shield radiation beams. In some embodiments, the MLC 500 may include a driving assembly configured to drive each leaf of the plurality of pairs of leaves to translate completely and (substantially) instantly from a first operative position to a second operative position. In some embodiments, the driving assembly may refer to the first drive mechanism illustrated in FIGS. 6A-7B, 10, and 11. In some embodiments, a leaf translates completely may mean that the translation of the leaf from a first position to a second position is directly finished. In some embodiments, a leaf translates (substantially) instantly may mean that the translation of the leaf from a first position to a second position is finished in a relatively short time (i.e., the leaf translates in a relatively high speed). In some embodiments, an operative position of a leaf may refer to a position at which the leaf is at an open state so that an aperture is formed.

In some embodiments, the MLC 500 may include a plurality of pairs of leaves configured to shield radiation beams. In some embodiments, the MLC 500 may include a driving assembly configured to drive each leaf of the plurality of pairs of leaves to translate from a first position where the plurality of pairs of leaves form a first aperture, to a second position where the plurality of pairs of leaves form a second aperture. In some embodiments, because the each leaf may translate at a relatively high speed, the first aperture may be changed to the second aperture non-gradually (i.e., at a relatively high speed). In some embodiments, the driving assembly may refer to the first drive mechanism illustrated in FIGS. 6A-7B, 10, and 11.

In some embodiments, the radiation system 100 may include a radiation source (e.g., the first radiation source 113). In some embodiments, the radiation system 100 may include an MLC 500. In some embodiments, the MLC 500 may include a plurality of pairs of leaves configured to shield radiation beams emitted from the radiation source. In some embodiments, the MLC 500 may include a driving assembly configured to drive one or more leaves of the plurality of pairs of leaves to move. In some embodiments, the driving assembly may include a driving sub-assembly configured to drive each leaf of the plurality of pairs of leaves to translate completely and (substantially) instantly from a first operative position to a second operative position during the radiation beams are off. In some embodiments, the driving assembly may include a position holding sub-assembly configured to maintain the each leaf in the first operative position or the second operative position during the radiation beams are on. In some embodiments, the driving sub-assembly may refer to the first drive mechanism illustrated in FIGS. 6A-7B, 10, and 11. In some embodiments, the position holding sub-assembly may refer to the stop block(s) illustrated in FIGS. 5-7B and 9-11 and/or the brake component(s) illustrated in FIGS. 6A-7B and 9-11.

It should be noted that the terms "first," "second," etc. are only for ease of description and do not represent a particular order or name. For example, a first target position of the leaf may not necessarily mean the first reached position of the leaf. As another example, the second target position of the leaf may not necessarily mean the second reached position of the leaf.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped in a single embodiment, figure, or descriptions thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A multi-leaf collimator, comprising:
a plurality of leaves configured to shield radiation beams, at least two leaves of the plurality of leaves being movable in a direction parallel to each another,
a plurality of stop blocks corresponding to the plurality of leaves, each stop block of the plurality of stop blocks being configured to define a position of a corresponding leaf of the plurality of leaves, and
a plurality of brake components releasably coupled to at least one leaf and configured to maintain a position of the at least one leaf when at least one corresponding stop block is moving,
wherein each leaf of at least some of the plurality of leaves is configured to be movable between at least two positions, at least one of the at least two positions being adjustable.

2. The multi-leaf collimator of claim 1, wherein at least some of the plurality of leaves are configured to move simultaneously while the radiation beams are off.

3. The multi-leaf collimator of claim 1, further comprising:
a first drive mechanism configured to actuate a movement of the each leaf from a first position to a second position.

4. The multi-leaf collimator of claim 3, wherein the first drive mechanism includes at least one of a pneumatic drive mechanism, a spring-based drive mechanism, or an electric-charge-based mechanism.

5. The multi-leaf collimator of claim 1, wherein the each stop block is movable, and each of the at least two positions of the corresponding leaf is adjustable by moving the each stop block.

6. The multi-leaf collimator of claim 5, further comprising:
a second drive mechanism configured to actuate the plurality of stop blocks to move.

7. The mufti-leaf collimator of claim 6, wherein the second drive mechanism includes a plurality of driving motors, each driving motor being configured to move at least one of the plurality of stop blocks to one or more target positions to define one or more positions of at least one corresponding leaf.

8. The multi-leaf collimator of claim 7, wherein the each driving motor being configured to move at least one of the plurality of stop blocks while the radiation beams are on.

9. The multi-leaf collimator of claim 1, further comprising:
a shield component configured to shield a first portion of the plurality of leaves such that a radiation beam is substantially blocked from passing through the first portion of the plurality of leaves.

10. The multi-leaf collimator of claim 9, being configured such that, when the radiation beam is on and the first portion of the plurality of leaves are shielded by the shield component, the first portion of the plurality of leaves are actuated to move and a second portion of the plurality of leaves are held still to allow passage of the radiation beam.

11. The multi-leaf collimator of claim 1, further comprising:
a shield component configured to shield a first portion of the plurality of leaves or a second portion of the plurality of leaves, the shield component being capable of switching between a first shielding position and a second shielding position, at the first shielding position the shield component shielding the first portion of the plurality of leaves, at the second shielding position the shield component shields the second portion of the plurality of leaves.

12. A multi-leaf collimator, comprising:
a plurality of pairs of leaves configured to shield radiation beams;
an actuator configured to drive at least one leaf of the plurality of pairs of leaves to translate among a first set of predefined positions at a first speed:
a positioner non-synchronically movable along with the actuator among a second set of predefined positions at a second speed slower than the first speed, the positioner being configured to place the at least one leaf at each of the first set of predefined positions; and
a position holder releasably coupled with the at least one leaf, the position holder being configured to maintain the at least one leaf at the each of the first set of predefined positions when the positioner is moving from a first predefined position of the second set of predefined positions to a second predefined position of the second set of predefined positions.

13. The multi-leaf collimator of claim 12, the positioner comprises a motor configured to drive the positioner to move at the second speed.

14. A multi-leaf collimator, comprising:
a plurality of pairs of leaves configured to shield radiation beams; and
a driving assembly configured to drive each leaf of the plurality of pairs of leaves to translate completely and substantially instantly from a first operative position to a second operative position;
a plurality of stop blocks corresponding to the plurality of pairs of leaves, each stop block of the plurality of stop blocks being configured to define a position of a corresponding leaf of the plurality of pairs of leaves; and a plurality of brake components releasably coupled to at least one leaf and configured to maintain a position of the at least one leaf when at least one corresponding stop block is moving, wherein each leaf of at least some of the plurality of pairs of leaves is configured to be movable between at least two positions, at least one of the at least two positions being adjustable.

15. The multi-leaf collimator of claim 14, wherein the driving assembly includes at least one of a pneumatic drive mechanism, a spring-based drive mechanism, or an electric-charge-based mechanism.

16. The multi-leaf collimator of claim 14, wherein the each stop block is movable, and the first operative position or the second operative position is adjustable by moving the each stop block.

17. The multi-leaf collimator of claim 14, further comprising:

a drive mechanism configured to actuate the plurality of stop blocks to move.

18. The multi-leaf collimator of claim 1, wherein the plurality of brake components include at least a fastening structure or a blocking structure.

19. The multi-leaf collimator of claim 1, wherein
at least one stop block of the plurality of stop blocks includes a protruding part,
at least one leaf of the plurality of leaves includes a notch set on an edge of the leaf, and
the protruding part of the at least one stop block and the notch set of the at least one leaf are configured to be operably coupled such that the at least one stop block restricts a movement of the at least one leaf.

20. The multi-leaf collimator of claim 1, wherein
at least one leaf of the plurality of leaves includes a protruding part,
at least one stop block of the plurality of stop blocks includes a notch set on an edge of the stop block, and
the protruding part of the at least one leaf and the notch set of the at least one stop block are configured to be operably coupled such that the at least one stop block restricts a movement of the at least one leaf.

* * * * *